US005758095A

United States Patent [19]
Albaum et al.

[11] Patent Number: 5,758,095
[45] Date of Patent: May 26, 1998

[54] INTERACTIVE MEDICATION ORDERING SYSTEM

[76] Inventors: David Albaum, 1423 Edris Dr., Los Angeles, Calif. 90035; Jeff Inokuchi, 1440 Cortez Ave., Burlingame, Calif. 94010; Denis Kitayama, 12140 Smokie La., Cerritos, Calif. 90701; Glen Wada, 20 S. 1300 East, Logan, Utah 84321-4940; Ray Wong, 900 Bush St. #1206, San Francisco, Calif. 94109-6399; Brian Komoto, 4029 W. School St., Visalia, Calif. 93291

[21] Appl. No.: 394,335

[22] Filed: Feb. 24, 1995

[51] Int. Cl.$^6$ ............... G06F 17/60; G06F 159/00; G06F 153/00

[52] U.S. Cl. ............... 395/202; 395/203; 395/226; 395/227; 395/769

[58] Field of Search ............ 364/401 M, 401 R, 364/413.01, 413.02; 395/202, 203, 226, 227, 768, 769, 785, 786

[56] References Cited

U.S. PATENT DOCUMENTS

| | | | |
|---|---|---|---|
| 4,036,462 | 7/1977 | Sheftel | 248/166 |
| 4,193,114 | 3/1980 | Benini | 395/213 |
| 4,525,775 | 6/1985 | Eydelman | 364/148 |

(List continued on next page.)

OTHER PUBLICATIONS

Dialog File 751, Acc. No. 00268373, Ez-Rx System, (Datapro Software Directory), record created Mar. 19, 1992, (first installed Feb. 1982).

Dialog File 256, Acc. No. 0107836, Ez-Rx System, released Feb. 1982, Softbase: Reviews, Companies, & Products.

Dialog File 149, Acc. No. 01480630, Ask Rx Plus (Evaluation) by K.H. Mosser & R.C. Glorioso, American Family Phys., v. 49, n. 6, p. 1548 May 1, 1994.

Dialog File 16, Acc. No. 05490260, Med. Tech. System Inc.; Health Bus. Sys. Inc. In Vivo the Bus & Med Report, Jan. 1995, p. 71.

Dialog File 187, Acc. No. 00143437, "The Pink Sheet", Feb. 5, 1996, vol. 58, Issue 6: Allscrips merger w/Physician Dispensing Systems . . . .

Medical Software Reviews, Jan. 1992/vol. 1, No. 1, Drug Interactions Software, by E.P. Hoffer, pp. 1-3.

Rebecca Coley: "Pharmacy Automation: Bitter Pills# or Spoonfuls of Sugar#", Healthcare Informatics, Jun. 1993, pp. 41-48.

Ask Rx, Drug Information Software for Microsoft® Windows™: 6-paged brochure, author & publication date unknown, software release date: 1992.

Dialog: File 237, Acc. No. 00015289; Ask Rx, Software Buyer's Guide & Product Description.

Dialog, File 148, Acc. No. 07511108; Ask Rx (Evaluation) by D. Nimouni & E. Blumenthal, Jul. 23, 1994, Lancet, v. 344, n 8917, p. 250.

Primary Examiner—Gail O. Hayes
Assistant Examiner—Joseph Thomas

[57] ABSTRACT

A system and method for ordering and prescribing drugs for a patient. This system includes an improved process for facilitating and automating the process of drug order entry. The user may interact with the system in a variety of ways such as keyboard, mouse, pen-base entry or voice entry. The system includes a database containing medical prescribing and drug information which is both general and patient-specific. The system also permits the user to view current and previously prescribed medications for any patient. The system can alert the user to potentially adverse situations as a result of the prescribed medication based on information in the database. The system also can automatically determine product selection based on descriptions and can automatically communicate the order to a pharmacy. Further, the system includes a means for automatically displaying messages to the user relating to predetermined situations. For example, such situations may include a medication which is not available in the formulary or the prescription of a non-recommended medication. The system streamlines the order entry process and makes information important to the drug ordering process easily available.

28 Claims, 82 Drawing Sheets

U.S. PATENT DOCUMENTS

| | | | |
|---|---|---|---|
| 4,576,184 | 3/1986 | Westerman | 128/733 |
| 4,604,690 | 8/1986 | Crabtree et al. | 395/653 |
| 4,625,275 | 11/1986 | Smith | 395/218 |
| 4,695,954 | 9/1987 | Rose et al. | 364/413.01 |
| 4,715,386 | 12/1987 | Martin | 128/733 |
| 4,766,542 | 8/1988 | Pilarczyk | 395/203 |
| 4,797,818 | 1/1989 | Cotter | 395/215 |
| 4,807,170 | 2/1989 | Kulli et al. | 364/715.01 |
| 4,825,869 | 5/1989 | Sasmor et al. | 607/27 |
| 4,837,719 | 6/1989 | McIntosh et al. | 364/569 |
| 4,839,806 | 6/1989 | Goldfischer et al. | 364/413.02 |
| 4,847,764 | 7/1989 | Halvorson | 364/413.02 |
| 4,853,521 | 8/1989 | Claeys et al. | 235/375 |
| 4,853,854 | 8/1989 | Behar et al. | 364/569 |
| 4,857,713 | 8/1989 | Brown | 395/203 |
| 4,878,175 | 10/1989 | Norden-Paul et al. | 395/202 |
| 4,916,611 | 4/1990 | Doyle, Jr. et al. | 395/202 |
| 4,918,604 | 4/1990 | Baum | 221/5 |
| 4,958,280 | 9/1990 | Pauly et al. | 395/203 |
| 4,958,284 | 9/1990 | Bishop et al. | 434/353 |
| 4,972,318 | 11/1990 | Brown et al. | 395/226 |
| 4,991,877 | 2/1991 | Lieberman | 283/36 |
| 4,992,940 | 2/1991 | Dworkin | 395/226 |
| 5,033,013 | 7/1991 | Kato et al. | 364/561 |
| 5,065,315 | 11/1991 | Garcia | 395/202 |
| 5,070,452 | 12/1991 | Doyle, Jr. et al. | 395/202 |
| 5,153,827 | 10/1992 | Coutré et al. | 364/413.02 |
| 5,175,681 | 12/1992 | Iwai et al. | 295/209 |
| 5,200,891 | 4/1993 | Kehr et al. | 221/2 |
| 5,200,905 | 4/1993 | Uemoto et al. | 364/474.04 |
| 5,208,762 | 5/1993 | Charhut et al. | 364/478.04 |
| 5,241,464 | 8/1993 | Greulich et al. | 395/226 |
| 5,243,998 | 9/1993 | Silverman et al. | 128/782 |
| 5,267,174 | 11/1993 | Kaufman et al. | 364/479.12 |
| 5,299,121 | 3/1994 | Brill et al. | 128/630 |
| 5,301,105 | 4/1994 | Cummings, Jr. et al. | 395/202 |
| 5,307,260 | 4/1994 | Watanabe et al. | 395/500 |
| 5,319,543 | 6/1994 | Wilhelm | 395/203 |
| 5,347,453 | 9/1994 | Maestre | 364/413.01 |
| 5,528,021 | 6/1996 | Lassus et al. | 235/380 |

Poetry Systems

11/18/94  13:00

ENTER I.D. AND SIGNATURE

| B | 7 | D | F | I |

_____
SIGNATURE

Poetry Systems

11/18/94  13:00

| | |
|---|---|
| Anderson, J | E327B |
| Blakemore, F | D321A |
| Henderson, R | C333B |
| Sanderson, S | D430B |
| Thomas, K | H221B |
| Zumwalt, L | D521A |

SELECT PATIENT:

D

| | | |
|---|---|---|
| Daren, Fred | C431 | 4958668573 |
| Derby, Martha | D224 | 6594858865 |
| Dien, Sarah | E448 | 4959538856 |
| Doe, Jane M | E321 | 5476345567 |
| Doe, John F | D231 | 4567535589 |
| Dohl, Michael | F356 | 5678864325 |
| Douglas, Tim | E332 | 5496568834 |
| Dow, Theresa | C443 | 3405968473 |
| Dunraht, Chris | E421 | 5049586685 |
| Dwyer, Henry | D330 | 6584778373 |

FIGURE 4

SELECT PATIENT:

| D | O | | | | | | | | | | | | | |
|---|---|---|---|---|---|---|---|---|---|---|---|---|---|---|

Doe, Jane M      E321    547634567
Doe, John F      D231    456753589
Dohl, Michael    F356    567864325
Douglas, Tim     E332    549656834
Dow, Theresa     C443    340596847

Poetry Systems

11/18/94   13:00

Anderson, J    E327B  D321A
Blakemore, F   D321A
Henderson, R   C333B
Sanderson, S   D430B
Thomas, K      H221B
Zumwalt, L     D521A

Poetry Systems

11/18/94  13:00

Anderson, J  E327B
Blakemore, F  D321A
Henderson, R  C333B
Sanderson, S  D430B
Thomas, K    H221B
Zumwalt, L   D521A

SELECT PATIENT:

| D | 2 | | | | | | | | | |

D221   Jones, Theodore     3495896686
D223   Franklin, Clarence  3508448437
D223B  Azama, Henry        2045968857
D224   Derby, Martha       6594858865
D230   Zumwalt, Jennifer   3059685974
D231A  Doe, John F         4567535589
D231B  Wong, Clarence S    6857473373
D234B  Grant, Keith        4696858847

SELECT PATIENT:

| D | 2 | 3 | 1 | | | | | | |

D231A Doe, John F          4567535890
D231B Wong, Clarence S     6857473730

Poetry Systems

11/18/94    13:00

Anderson, J   E327B
Blakemore, F  D321A
Henderson, R  C333B
Sanderson, S  D430B
Thomas, K     H221B
Zumwalt, L    D521A

SELECT PATIENT:

| 4 | 5 | 6 | | | | | | |
|---|---|---|---|---|---|---|---|---|

456156754 Jones, Theodore      D523A
456378689 Franklin, Clarence   E465B
456753589 Doe, John F          D231A
456867854 Taylor, Cynthia R    D564B
456906789 Grant, Keith         F347A

Poetry Systems

11/18/94  13:00

Anderson, J    E327B
Blakemore, F   D321A
Henderson, R   C333B
Sanderson, S   D430B
Thomas, K      H221B
Zumwalt, L     D521A

FIGURE 8

Doe, John F   D231A   45675353589

[NEW] [DC] [EDIT] [LIST] [OPEN]   Allergies NKA

Poetry Systems

11/18/94  13:00
SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

ERASE    MESSAGES
1. Do you want peak and trough levels for the gentamicin?
2. Do you want to order a KCL scale?

ORDERS to COUNTERSIGN/ [RENEW]
40mEq po KCl now
11/17/94 1345  J.Williams,RN/

Digoxin 0.25mg iv q2h x 2 doses
11/17/94 1530  B.Thompson,RN/

FIGURE 9

Poetry Systems

11/18/94 13:00

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

Doe, John F  D231A  456753589

NEW  DC  EDIT  LIST  OPEN  Allergies NKA

ERASE  MESSAGES / RENEW

1. Do you want peak and trough levels for the gentamicin?
2. Do you want to order a KCL scale?

FIGURE 10

Doe, John F    D231A    456753589

| NEW | DC | EDIT | LIST | OPEN | Allergies NKA |

ORDER    MESSAGE    ANNOTATION

Poetry Systems

11/18/94    13:00

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

Poetry Systems

Doe, John F    D231A    456753589

| NEW | DC | EDIT | LIST | OPEN |

Allergies: NKA

11/18/94  13:00

SCHEDULED meds
1. Lasix 20mg po bid
2. KCl 20mEq po bid

PRN medications
3. MS 2mg iv q4h prn
4. Tyl#3 1-2tabs po q4-6h prn
5. Phenergan 25mg im\iv q4-6h prn

PRESENT ACTIONS
KEFZOL 1GM IV Q8H

NEW ORDER ENTRY    VIEW

| K | E | F | Z | O | L | 1 | G | M | I | V | Q | 8 | H |

Orders authorized by: ___

80

Poetry Systems

11/18/94  13:00

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

Doe, John F     D231A     456753589

[NEW] [DC] [EDIT] [LIST] [OPEN]     Allergies SPECIFIED pneumonia        4|5         5-11        7|0
DIAGNOSIS        AGE      HEIGHT      WEIGHT
                          (FT-IN)       (KGS)

ALLERGIES
  DRUG

PENICILLIN

ADVERSE REACTION

RASH

Doe, John F   D231A   456753589

| NEW | DC | EDIT | LIST | OPEN | Allergies NKA |

NEW ORDER ENTRY                      VIEW

Poetry Systems

11/18/94   13:00

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

FIGURE 14

Poetry Systems

11/18/94  13:00

SCHEDULED meds

PRN medications

PRESENT ACTIONS

CEFAZOLIN 1gm

Doe, John F    D231A    456753589

| NEW | DC | EDIT | LIST | OPEN |

Allergies
NKA

NEW ORDER ENTRY

K E F Z O L                                      VIEW — 85

| 1 | CEFAZOLIN | 500mg | $ 2.75 |
| 2 | CEFAZOLIN | 1gm | $ 5.20 |
| 3 | CEFAZOLIN (Kefzol,Ancef) | 1gm | $ 6.35 |
| 4 | CEFOTETAN | 1gm | $ 9.95 |
| 5 | CEFOTETAN | 2gm | $ 6.25 |
| 6 | CEFOTETAN (Cefotan) | | |
| 7 | CEFOTAXIME | 1gm | $ 6.25 |
| 8 | CEFOTAXIME | 2gm | $ 9.99 |
| 9 | CEFOTAMIME (Clafloran) | | |
| 10 | CEFTAZIDIME | 1gm | $10.20 |

Poetry Systems

Doe, John F  D231A  4567533589

11/18/94  13:00

SCHEDULED meds

PRN medications

PRESENT ACTIONS

CEFAZOLIN 1gm

NEW | DC | EDIT | LIST | OPEN

Allergies
NKA

NEW ORDER ENTRY  VIEW

CEFAZOLIN  1 g m

88

Poetry Systems

Doe, John F    D231A    456753589

| NEW | DC | EDIT | LIST | OPEN | Allergies NKA |

11/18/94  13:00

SCHEDULED meds

PRN medications

PRESENT ACTIONS
CEFAZOLIN 1gm IV
Q8H

NEW ORDER ENTRY    VIEW

| C | E | F | A | Z | O | L | I | N | 1 | g | m | I | V |
| Q | 8 | H | | | | | | | | | | | |

Doe, John F    D231A    456753589

[NEW] [DC] [EDIT] [LIST] [OPEN]    Allergies
                                   NKA

NEW ORDER ENTRY

K E F Z O L                        [VIEW]

1. CEFAZOLIN            500mg    $ 2.75
2. CEFAZOLIN            1gm      $ 5.20
3. CEFAZOLIN (Kefzol,Ancef)
4. CEFOTETAN            1gm      $ 6.35
5. CEFOTETAN            2gm      $ 9.95
6. CEFOTETAN (Cefotan)
7. CEFOTAXIME           1gm      $ 6.25
8. CEFOTAMIME           2gm      $ 9.99
9. CEFOTAMIME (Claforan)
10. CEFTAZIDIME         1gm      $10.20

92

Poetry Systems

11/18/94   13:00

SCHEDULED meds
1. Lasix 20mg po bid
2. KCl  20mEq po bid

PRN medications
3. MS 2mg iv q4h prn
4. Tyl#3 1-2tabs po q4-6h prn
5. Phenergan 25mg im\iv q4-6h prn PRESENT ACTIONS
CEFTAZIDIME 1gm

FIGURE 18

Doe, John F    D231A    4567753589

| NEW | DC | EDIT | LIST | OPEN |

Allergies: NKA

Poetry Systems

11/18/94   13:00

SCHEDULED meds
[1] Lasix 20mg po bid
[2] KCl 20mEq po bid

PRN medications
[3] MS 2mg iv q4h prn
[4] Tyl#3 1-2tabs po q4-6h prn
[5] Phenergan 25mg im\iv q4-6h prn PRESENT ACTIONS
CEFTAZIDIME 1gm

NEW ORDER ENTRY    VIEW

Doe, John F    D231A    4567553589

| NEW | DC | EDIT | LIST | OPEN | Allergies NKA |

NEW ORDER ENTRY                           VIEW

CEFTAZIDIME    1 gm
IV  Q8H

Poetry Systems

11/18/94    13:00

SCHEDULED meds
1. Lasix 20mg po bid
2. KCl 20mEq po bid

PRN medications
3. MS 2mg iv q4h prn
4. Tyl#3 1-2tabs po q4-6h prn
5. Phenergan 25mg im\iv q4-6h prn PRESENT ACTIONS
CEFTAZIDIME 1gm
IV Q8H

Poetry Systems

Doe, John F   D231A   456753589

| NEW | DC | EDIT | LIST | OPEN |

Allergies NKA

11/18/94   13:00

SCHEDULED meds
1. Lasix 20mg po bid
2. KCl 20mEq po bid
3. Ampicillin 1gm iv q4h
4. Gentamicin 120mg iv q12h PRN medications

PRESENT ACTIONS

MAXZIDE 1 PO QD

NEW ORDER ENTRY          VIEW

| M A X Z I D E | 1 | P O | Q D |

This drug is not on the hospital formulary.

1. Substitute Dyazide for Maxzide.
2. Special order requested.
3. Instruct patient to take own medication supply.

| | | | | | Poetry Systems |
|---|---|---|---|---|---|
| Doe, John F   D231A   4567533589 | | | | | 11/18/94  13:00 |
| NEW | DC | EDIT | LIST | OPEN | SCHEDULED meds |
| Allergies NKA | | | | | PRN medications |
| | | | | | PRESENT ACTIONS |
| NEW ORDER ENTRY | | | | VIEW | K |
| K | C | L |   | 2 | 0 | m | E | q |   | p | o |   | T | I | D | D/C Ampicillin |
| F | u | r | o | s | e | m | i | d | e |   | 2 | 0 | m | g | | D/C Gentamicin |
| p | o |   | B | I | D | | | | | | | | | | | Furosemide 20mg po BID |
| D | / | C |   | G | E | N | T | A | M | I | C | I | N | | | KCl 20mEq po TID |
| D | / | C |   | A | M | P | I | C | I | L | L | I | N | | | |
| K | | | | | | | | | | | | | | | | |

Doe, John F    D231A    456753589

[NEW] [DC] [EDIT] [LIST] [OPEN]    Allergies
                                    NKA

Poetry Systems

11/18/94  13:00

SCHEDULED meds
1. Lasix 20mg po bid
2. KCl 20mEq po bid

PRN medications
1. MS 2mg iv q4h prn
2. Tyl#3 1-2tabs po q4-6h prn
3. Phenergan 25mg im\iv q4-6h prn PRESENT ACTIONS
Cefoxitin 1gm iv q6h

NEW ORDER ENTRY                [VIEW]

| C | E | F | O | X | I | T | I | N | 1 | G | M | Q | 6 | H |

In accordance with recommendations from the Antibiotic Selection Committee, the Pharmacy and Therapeutics Commitee has removed Cefoxitin from the formulary. Cefotetan is therapeutically equivalent.

☐ 1 Substitute CEFOTETAN 1gm IV q12h for CEFOXITIN 1gm IV q6h.
☐ 2 Substitute CEFOTETAN 2gm IV q12h for CEFOXITIN 2gm IV q6h.
☐ 3 Request special CEFOXITIN order.

Doe, John F    D231A    456753589

[NEW] [DC] [EDIT] [LIST] [OPEN]    Allergies NKA

NEW ORDER ENTRY    [VIEW]

| P | H | E | N | E | R | G | A | N | 2 | 5 | m | g |
| I | M | / | P | O | / | P | R | Q | 4 | - | 6 | H |
| P | R | N | | | | | | | | | | |

Poetry Systems

11/18/94  13:00

SCHEDULED meds
1. Lasix 20mg po bid
2. KCl 20mEq po bid

PRN medications
3. MS 2mg iv q4h prn
4. Tyl#3 1-2tabs po q4-6h prn
5. Phenergan 25mg im\iv q4-6h prn PRESENT ACTIONS
PHENERGAN 25mg
IM/PO/PR Q4-6H PRN

FIGURE 24

Poetry Systems

Doe, John F   D231A   456753589

11/18/94   13:00

Allergies: NKA

[NEW] [DC] [EDIT] [LIST] [OPEN]

SCHEDULED meds
1. Lasix 20mg po bid
2. KCl 20mEq po bid
3. Ampicillin 1gm iv q4h
4. Gentamicin 120mg iv q12h PRN medications

PRESENT ACTIONS
DECADRON TAPER

NEW ORDER ENTRY   [VIEW]

DECADRON TAPER

Doe, John F    D231A    45675353589

| NEW | DC | EDIT | LIST | OPEN |

Allergies
NKA

Poetry Systems

11/18/94    13:00

SCHEDULED meds
1. Lasix 20mg po bid
2. KCl 20mEq po bid
3. Ampicillin 1gm iv q4h
4. Gentamicin 120mg iv q12h PRN medications

PRESENT ACTIONS
DECADRON TAPER

NEW ORDER ENTRY    VIEW

D E C A D R O N   T A P E R

| DATE | DOSE and ROUTE | | |
|---|---|---|---|
| 11/21 | 4 mg | po/iv | q 6h |
| 11/23 | | | |
| 11/24 | 3 mg | po/iv | q 6h |
| 11/27 | | | |
| 11/28 | 2 mg | po | |
| 11/29 | | | |
| 11/30 | 1 mg | po | qd |

| Doe, John F | D231A | 4567535589 | | |
|---|---|---|---|---|
| NEW | DC | EDIT | LIST | OPEN |

Allergies NKA

Poetry Systems

11/18/94  13:00

SCHEDULED meds
1. Lasix 20mg po bid
2. KCl 20mEq po bid
3. Ampicillin 1gm iv q4h
4. Gentamicin 120mg iv q12h PRN medications

PRESENT ACTIONS

TPN
TPN-Pepcid 40 mg/d
TPN-Insulin 10 u/l

NEW ORDER ENTRY                                    VIEW

T P N

TOTAL PARENTERAL NUTRITION

☐ Renew previous order
DEXTROSE ___ %         AMINO ACIDS ___ %
NaCl ___ mEq           KCl ___ mEq
NaAcet ___ mEq         KAcet ___ mEq
NaPhos ___ mEq         KPhos ___ mEq
MgSulf ___ mEq         CaGluc ___ mEq
MVI ___ unit
Trace El ___ ml        Pepcid  40  mg/day
Insulin  10  un/l      Heparin ___ un/l
Other:

Doe, John F    D231A    4567533589

Poetry Systems

NEW | DC | EDIT | LIST | OPEN    Allergies NKA

146

11/18/94    13:00

SCHEDULED meds
1. Lasix 20mg po bid
2. KCl 20mEq po bid
3. Kefzol 1gm IV q8H

PRN medications
4. MS 2mg iv q4h prn
5. Tyl#3 1-2tabs po q4-6h prn
6. Phenergan 25mg im\iv q4-6h prn PRESENT ACTIONS
D/C Kefzol ERASE    MESSAGES
1. Do you want peak and trough levels for the gentamicin?
2. Do you want to order a KCL scale?

ORDERS to COUNTERSIGN/ RENEW
40mEq po KCl now
11/17/94 1345  J.Williams,RN/

Digoxin 0.25mg iv q2h x 2 doses
11/17/94 1530  B.Thompson,RN/

FIGURE 29

Poetry Systems

11/18/94    13:00

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

Doe, John F    D231A    456753589

[NEW] [DC] [EDIT] [LIST] [OPEN]    Allergies NKA

Display all Current Meds
Display all Antibiotics
Display all PAST Meds

Display CURRENT Scheduled Meds
Display PAST Scheduled Meds

Display CURRENT PRN Meds
Display PAST PRN Meds

Doe, John F    D231A    4567533589      Poetry Systems

| NEW | DC | EDIT | LIST | OPEN |

Allergies: NKA

11/18/94    13:00

PAST SCHEDULED MEDS
| MED REGIMEN | START | STOP |
|---|---|---|
| Lasix 40mg po bid | 11/03 | 11/04 |
| Lasix 20mg po tid | 11/04 | 11/06 |
| Cefotetan 1gm iv q12h | 11/03 | 11/10 |
| Ranitidine 50mg iv q8h | 11/93 | 11/07 |

158

PAST PRN MEDS

FIGURE 31

Poetry Systems

Doe, John F    D231A    456753589

[NEW] [DC] [EDIT] [LIST] [OPEN]    Allergies SPECIFIED

11/18/94  13:00

SCHEDULED meds
1. Lasix 20mg po bid
2. KCl 20mEq po bid

PRN medications
3. MS 2mg iv q4h prn
4. Tyl#3 1-2tabs po q4-6h prn
5. Phenergan 25mg im\iv q4-6h prn

PRESENT ACTIONS
PCN 2MU IV Q4H

NEW ORDER ENTRY

| P | C | N | 2 | M | U | | I | V | | Q | 4 | H | | [VIEW] |

A potential drug allergy has been recognized.

☐ Discontinue order.

☐ Proceed with order as written.

Poetry Systems

11/18/94   13:00

SCHEDULED meds
1. Lasix 20mg po bid
2. KCl 20mEq po bid

PRN medications
3. MS 2mg iv q4h prn
4. Tyl#3 1-2tabs po q4-6h prn
5. Phenergan 25mg im\iv q4-6h prn PRESENT ACTIONS
CAPOTEN 15mg TID Doe, John F    D231A    456753589

[NEW] [DC] [EDIT] [LIST] [OPEN]    Allergies SPECIFIED

NEW ORDER ENTRY                              [VIEW]

| C | A | P | O | T | E | N |  | 1 | 5 | m | g | , | T | I | D |

Please verify the drug dosage.
This drug is available as a scored tablet in the following strengths:

12.5 mg, 25 mg, 50 mg

NEW DOSE  [          ]

☐ Proceed with order as written.

Doe, John F  D231A  456753589

[NEW] [DC] [EDIT] [LIST] [OPEN]  Allergies NKA

Poetry Systems

11/18/94  13:00

SCHEDULED meds
1. Lasix 20mg po bid
2. KCl 20mEq po bid
3. Digoxin 0.25mg qd

PRN medications
4. MS 2mg iv q4h prn
5. Tyl#3 1-2tabs po q4-6h prn
6. Phenergan 25mg im\iv q4-6h prn PRESENT ACTIONS
Verapamil 80mg po tid

NEW ORDER ENTRY  [VIEW]

A potential interaction has been reported between the following drug combinations:   [display]

Digoxin - Verapamil

Poetry Systems

11/18/94    13:00

SCHEDULED meds
① Lasix 20mg po bid
② KCl 20mEq po bid
③ Digoxin 0.25mg qd

PRN medications
④ MS 2mg iv q4h prn
⑤ Tyl#3 1-2tabs po q4-6h prn
⑥ Phenergan 25mg im\iv q4-6h prn

PRESENT ACTIONS
GENTAMICIN 80MG
IV Q8H

Doe, John F    D231A    456753589

[NEW] [DC] [EDIT] [LIST] [OPEN]    Allergies NKA

NEW ORDER ENTRY    [VIEW]

| G | E | N | T | A | M | I | C | I | N | | 8 | 0 | M | G |

Pharmacokinetic predictions based on patient variables (ht,wt,age) and renal function (Clcr, CR trends) suggest the following dose:

| G | E | N | T | A | M | I | C | I | N | | 1 | 3 | 0 | |
| M | G | | I | V | | Q | 1 | 2 | H | | | | | |

☐ Accept new dose recommendations.
☐ Process original order as written.

Doe, John F    D231A    456753589

| NEW | DC | EDIT | LIST | OPEN | | Allergies NKA |

Poetry Systems

11/18/94   13:00

SCHEDULED meds
1. Lasix 20mg po bid
2. KCl 20mEq po bid
3. Digoxin 0.25mg qd

PRN medications
1. MS 2mg iv q4h prn
2. Tyl#3 1-2tabs po q4-6h prn
3. Phenergan 25mg im\iv q4-6h prn PRESENT ACTIONS
AZID 150mg po BID

NEW ORDER ENTRY                    VIEW

| A | Z | I | D | | 1 | 5 | 0 | mg | po | BID |

This is an unrecognized drug name.
Please select from the following:

1. AXID    (H-2 blocker, 150/300mg cap)
2. ANSAID  (NSAID, 50/100mg tab)

3. Proceed with order as written.

Poetry Systems

Doe, John F  D231  456753589

Allergies: NKA

[NEW] [DC] [EDIT] [LIST] [OPEN]

11/18/94  13:00

SCHEDULED meds
1. Lasix 20mg po bid
2. KCl 20mEq po bid
3. Ampicillin 1gm iv q4h
4. Gentamicin 120mg iv q12h
5. Clindamycin 900mg iv q8h
6. Digoxin 0.125mg po qd PRN medications

PRESENT ACTIONS

NEW ORDER ENTRY  [VIEW]

Poetry Systems

Doe, John F    D231A    456753589

| NEW | DC | EDIT | LIST | OPEN |

Allergies: NKA

11/18/94  13:00

SCHEDULED meds

PRN medications
1. MS 2mg iv q4h prn
2. Tyl#3 1-2tabs po q4-6h prn
3. Phenergan 25mg im\iv q4-6h prn

PRESENT ACTIONS

K
D/C Ampicillin
D/C Gentamicin
Furosemide 20mg po BID
KCl 20mEq po TID

NEW ORDER ENTRY    VIEW

| K | C | L |   | 2 | 0 | m | E | q |   | p | o |   | T | I | D |
| F | u | r | o | s | e | m | i | d | e |   | 2 | 0 | m | g |   |
| p | o |   | B | I | D |   |   |   |   |   |   |   |   |   |   |
| D | / | C |   | A | M | P | I | C | I | L | L | I | N |   |   |
| D | / | C |   | G | E | N | T | A | M | I | C | I | N |   |   |
| K |   |   |   |   |   |   |   |   |   |   |   |   |   |   |   |

FIGURE 39

Poetry Systems

Doe, John F    D231A    4567753589    Allergies NKA

[NEW] [DC] [EDIT] [LIST] [OPEN]

11/18/94  13:00

SCHEDULED meds
1. Lasix 20mg po bid
2. KCl 20mEq po bid
3. Digoxin 0.25mg qd
4. Kefzol 1gm iv q8h
5. ASA 325mg po qd PRN medications
6. MS 2mg iv q4h prn
7. Tyl#3 1-2tabs po q4-6h prn
8. Phenergan 25mg im\iv q4-6h prn

PRESENT ACTIONS

NEW ORDER ENTRY    [VIEW]

RX

TAKE HOME MEDICATIONS                                No.

| L | a | s | i | x |   | 2 | 0 | m | g |   | p | o |   | b | i | d |   |   |   |   |   | 3 | 0 |
| K | C | l |   | 2 | 0 | m | E | q |   | p | o |   | b | i | d |   |   |   |   |   |   | 3 | 0 |
| T | y | l | # | 3 |   | 1 | - | 2 |   | t | a | b | s |   | p | o |   |   |   |   |   | 2 | 0 |
| q | 4 | - | 6 | h |   | p | r | n |   |   |   |   |   |   |   |   |   |   |   |   |   |   |   |

Doe, John F    D231A    456753589

| NEW | DC | EDIT | LIST | OPEN | Allergies NKA |

NEW ORDER ENTRY    [VIEW]

POST PARTUM

Poetry Systems

11/18/94  13:00
SCHEDULED meds
PRN medications
PRESENT ACTIONS
POST PARTUM

Doe, John F   D231A   456753589

[NEW] [DC] [EDIT] [LIST] [OPEN]   Allergies NKA

Poetry Systems

11/18/94  13:00

SCHEDULED meds

PRN medications

PRESENT ACTIONS

DSS 250mg po bid
TYLENOL 650mg po
q6h prn
METHERGINE 0.2mg
po q4h prn
TYLENOL #3 1-2
tab po q4-6h prn
METAMUCIL 1 pkt
po bid
Demerol 25-50mg

NEW ORDER ENTRY   [VIEW]

| D | S | S |   | 2 | 5 | 0 | m | g |   | p | o |   | b | i | d |
| T | Y | L | E | N | O | L |   | 6 | 5 | 0 | m | g |   | p | o |
| q | 6 | h |   | p | r | n |   |   |   |   |   |   |   |   |   |
| M | E | T | H | E | R | G | I | N | E |   | 0 | . | 2 | m | g |
| p | o |   | q | 4 | h |   | p | r | n |   |   |   |   |   |   |
| T | Y | L | E | N | O | L |   | # | 3 |   | 1 | - | 2 |   |   |
| t | a | b |   | p | o |   | q | 4 | - | 6 | h |   | p | r | n |

Poetry Systems

11/18/94  13:00

SCHEDULED meds
1. Lasix 20mg po bid
2. KCl 20mEq po bid
3. Digoxin 0.25mg qd
4. CEFTAZIDIME 1gm IV Q8H PRN medications
5. MS 2mg iv q4h prn
6. Tyl#3 1-2tabs po q4-6h prn

PRESENT ACTIONS

Doe, John F    D231A    456753589

NEW | DC | EDIT | LIST | OPEN

Allergies
NKA

NEW ORDER ENTRY    VIEW

Doe, John F    D231A    4567533589

[NEW] [DC] [EDIT] [LIST] [OPEN]    Allergies NKA

Poetry Systems

11/18/94  13:00

SCHEDULED meds
1. Lasix 20mg po bid
2. KCl 20mEq po bid
3. Digoxin 0.25mg qd

PRN medications
4. MS 2mg iv q4h prn
5. Tyl#3 1-2tabs po q4-6h prn

PRESENT ACTIONS

CEFTAZIDIME
IV Q8H

NEW ORDER ENTRY    [VIEW]

Poetry Systems

Doe, John F    D231A    4567533589

| NEW | DC | EDIT | LIST | OPEN | Allergies NKA |

11/18/94   13:00

SCHEDULED meds
1. Lasix 20mg po bid
2. KCl 20mEq po bid
3. Digoxin 0.25mg qd

PRN medications
4. MS 2mg iv q4h prn
5. Tyl#3 1-2tabs po q4-6h prn

PRESENT ACTIONS
CEFTAZIDIME 2gm
IV Q8H

NEW ORDER ENTRY    VIEW

CEFTAZIDIME    2 gm
IV Q8H

FIGURE 45

Doe, John F   D231A   456753589

[NEW] [DC] [EDIT] [LIST] [OPEN]   Allergies NKA

NEW ORDER ENTRY

| I | M | I | P | E | N | E | M |   | 5 | 0 | 0 | m | g |

[VIEW]

The Pharmacy and Therapeutics Committee has placed this antibiotic in the restricted category. Approval for use by the Infectious Disease Service (ID) is required.

[1] Process this order as written. ID approval HAS been obtained.
[2] Process this order as written. ID approval HAS NOT been obtained.
[3] Cancel this order.

Poetry Systems

11/18/94   13:00

SCHEDULED meds
[1] Lasix 20mg po bid
[2] KCl 20mEq po bid
[3] Digoxin 0.25mg qd

PRN medications
[1] MS 2mg iv q4h prn
[2] Tyl#3 1-2tabs po q4-6h prn

PRESENT ACTIONS
IMIPENEM 500mg iv q6h

Poetry Systems

Doe, John F   D231A   456753589

11/18/94   13:00

Allergies NKA

[NEW] [DC] [EDIT] [LIST] [OPEN]

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

NEW ORDER ENTRY   [VIEW]

Poetry Systems

11/18/94  13:00

SCHEDULED meds
1. Lasix 20mg po bid
2. KCl 20mEq po bid
3. Ampicillin 1gm iv q4h
4. Gentamicin 120mg iv q12h PRN medications
5. MS 2mg iv q4h prn
6. Tyl#3 1-2tabs po q4-6h prn
7. Phenergan 25mg im\iv q4-6h prn

PRESENT ACTIONS

Doe, John F    D231A    456753589

[NEW] [DC] [EDIT] [LIST] [OPEN]    Allergies NKA

NEW ORDER ENTRY    [VIEW]

L I S I N O P R I L *

Lisinopril (Zestril, Prinivil)
Classification: angiotensin converting enzyme inhibitor

DRUG INFORMATION DATABASE

FIGURE 48

Doe, John F    D231A    456753589

[NEW] [DC] [EDIT] [LIST] [OPEN]    Allergies
                                    NKA Increasing serum creatinine values suggest
a declining trend in renal function.
The serum K+ level is elevated.

| Date  | 11/18 | 11/16 | 11/14 | 11/09 | 11/04 |
|-------|-------|-------|-------|-------|-------|
| Creat | 2.4   | 1.9   | 1.6   | 1.4   | 0.9   |
| K+    | 5.6   | 5.2   | 4.5   | 4.5   | 4.2   |

DRUG/DOSE ALERTS:

Digoxin is eliminated primarily by the
kidneys. Conservative dosing and serum
level monitoring is recommended.

Serum K+ elevation is evident. Please
re-evaluate present dose.

Poetry Systems

11/18/94  13:00

SCHEDULED meds
1. Lasix 20mg po bid
2. KCl  20mEq po bid
3. Digoxin 0.25mg qd

PRN medications
4. MS 2mg iv q4h prn
5. Tyl#3 1-2tabs po
   q4-6h prn
6. Phenergan 25mg
   im\iv q4-6h prn

PRESENT ACTIONS

Doe, John F  45675389  Blue Cr/MC  Poetry Systems

NEW | DC | EDIT | LIST | OPEN | 11/18/94  13:00

Allergies
NKA

ACTIVE PRESCRIPTIONS — 90
1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS — 91

PRESENT ACTIONS

ERASE  MESSAGES

Doe, John F  456753589  Blue Cr/MC   Poetry Systems

| NEW | DC | EDIT | LIST | OPEN |

Allergies: NKA    11/18/94  13:00

ACTIVE PRESCRIPTIONS

1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS

PRESENT ACTIONS

MESSAGES  | ERASE |

1. Prescription for Digoxin renewed on 11/12/94 was not picked up.
2. Dr. Schmidt, cardiologist, started ASA 325mg daily (entered into ACTIVE MEDICATIONS listing).

Doe, Jane M  54763456 7  MC  Poetry Systems

[NEW] [DC] [EDIT] [LIST] [OPEN]   11/18/94   13:00

Allergies
NKA

| NEW PRESCRIPTION ENTRY [VIEW] | ACTIVE PRESCRIPTIONS |
|---|---|
| | INACTIVE PRESCRIPTIONS |
| | PRESENT ACTIONS |
| | CIPRO 500MG PO BID |

Prescribing this drug for Medi-CAL patients is restricted to a limited number of pre-approved indications. For non-approved indications, a Treatment Authorization Request (TAR) is required.

[1] CANCEL this order.

[2] PROCESS this order. Treatment is for a pre-approved indication (chronic pylonephritis, osteomyelitis).

[3] PROCESS this order. Requesting authorization (TAR) for treating pneumonia or a gastrointestinal infection.

FIGURE 54

Doe, John F  456753589  Blue Cr/MC    Poetry Systems

[NEW] [DC] [EDIT] [LIST] [OPEN]    11/18/94  13:00

Allergies
NKA

ACTIVE PRESCRIPTIONS
1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain Digoxin 0.25mg po qd    #100    x4
started: 02/17/92  J. Jones, MD
changed: 05/13/94  J. Jones, MD
Dosing History:
02/17/92-04/19/93    0.125mg po qd
04/19/93-05/13/94    0.125/0.25mg alt qod

ANNOTATIONS

05/13/94  2+ pitting ankle edema
          HR 87, 150/85, CR 1.2

05/01/94  0.7 ng/ml (Fremont Lab)

04/19/93  3+ pitting ankle edema
          HR 92  145/89

KOMOTO'S PHARMACY    805-725-3640

INACTIVE PRESCRIPTIONS

PRESENT ACTIONS

Doe, Jane M    457634567    MC

| NEW | DC | EDIT | LIST | OPEN |

Allergies NKA

Poetry Systems

11/18/94    13:00

ACTIVE PRESCRIPTIONS

1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS

PRESENT ACTIONS

NEW PRESCRIPTION ENTRY    VIEW

| A | C | C | U | P | R | I | L | 1 | 0 | m | g |   |
| p | o |   | Q | D |   |   |   | 1 | 0 | 0 | x | 5 |

FIGURE 56

Poetry Systems

Doe, Jane M  54763 4567  MC   11/18/94  13:00

| NEW | DC | EDIT | LIST | OPEN |

Allergies
NKA

ACTIVE PRESCRIPTIONS

INACTIVE PRESCRIPTIONS

PRESENT ACTIONS

ACCUPRIL 10MG po QD

NEW PRESCRIPTION ENTRY  VIEW

This drug is not on the Medi-CAL formulary. Prescribing this drug requires a pre-approved Treatment Authorization Request (TAR) to be on file.

1. CANCEL this order.

2. PROCESS this order. A pre-approved TAR is on file.

3. PROCESS this order. The patient is willing to incur expenses and knows tha Medi-CAL will not pay reimbursement.

4. SUBSTITUTE with one of the following formulary drugs: CAPTOPRIL , ENALAPRIL , FOSINOPRIL , BENAZEPRIL

FIGURE 57

Doe, Jane M    54763454567    MC

| NEW | DC | EDIT | LIST | OPEN |

Allergies
NKA

Poetry Systems

11/18/94    13:00

ACTIVE PRESCRIPTIONS

1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS

PRESENT ACTIONS

NEW PRESCRIPTION ENTRY    VIEW

Doe, John F   456753589   Blue Cr/MC   Poetry Systems

| NEW | DC | EDIT | LIST | OPEN | Allergies NKA | 11/18/94   13:00 |

ACTIVE PRESCRIPTIONS
1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS

PRESENT ACTIONS

ORDER  MESSAGES  ANNOTATIONS

Starting ASA in place of coumadin.
I will evaluate patient at 4 mo
intervals.   Charles Schmidt, MD

FIGURE 59

Doe, John F  456753589  Blue Cr/MC    Poetry Systems

| NEW | DC | EDIT | LIST | OPEN |   Allergies NKA   11/18/94  13:00

ACTIVE PRESCRIPTIONS
1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS

PRESENT ACTIONS

NEW PRESCRIPTION ENTRY | VIEW

FIGURE 60

Doe, John F  D231A  456753589

| NEW | DC | EDIT | LIST | OPEN |

Allergies NKA

Poetry Systems

11/18/94  13:00

SCHEDULED meds
1. Lasix 20mg po bid
2. KCl 20mEq po bid
3. Ampicillin 1gm iv q4h
4. Gentamicin 80mg iv q8h PRN medications
5. MS 2mg iv q4h prn
6. Tyl#3 1-2tabs po q4-6h prn
7. Phenergan 25mg im\iv q4-6h prn

PRESENT ACTIONS

| ORDER | MESSAGE | ANNOTATION |

FIGURE 61

Doe, John F    D231A    456753589    Allergies NKA

[NEW] [DC] [EDIT] [LIST] [OPEN]

Poetry Systems

11/18/94    13:00

SCHEDULED meds
1. Lasix 20mg po bid
2. KCl 20mEq po bid
3. Ampicillin 1gm iv q4h
4. Gentamicin 80mg iv q8h PRN medications
5. MS 2mg iv q4h prn
6. Tyl#3 1-2tabs po q4-6h prn
7. Phenergan 25mg im\iv q4-6h prn

PRESENT ACTIONS

[ORDER] [MESSAGE] [ANNOTATION]

11/18/94   Gentamicin 80mg iv q8h
           peak=4.7  trough=2.5
           recommend change to 120mg q12h
           D. Kitayama, Pharm.D.

FIGURE 62

Doe, John F   D231A   456753589

| NEW | DC | EDIT | LIST | OPEN |

Allergies: NKA

Poetry Systems

11/18/94   13:00

SCHEDULED meds
1. Lasix 20mg po bid
2. KCl 20mEq po bid
3. Ampicillin 1gm iv q4h
4. Gentamicin 120mg iv q12h Gentamicin 120mg iv q12h
started: 11/16/94   J. Jones, MD
changed: 11/18/94   J. Jones, MD
Dosing History:
11/16/94-11/18/94   80mg iv q8h
11/18/94-present    120mg iv q12h PRN medications
5. MS 2mg iv q4h prn
6. Tyl#3 1-2tabs po q4-6h prn
7. Phenergan 25mg im\iv q4-6h prn

ANNOTATIONS

11/18/94 Gentamicin: 80mg iv q8h
peak=4.7 trough=2.5
recommend change to 120mg iv q12h
D.Kitayama, Pharm.D.

PRESENT ACTIONS

FIGURE 63

| CIPROFLOXACIN | MC |

(Dose, Route, Frequency)

Prescribing this drug for Medi-CAL patients is restricted to a limited number of pre-approved indications. For non-approved indications, a Treatment Authorization Request (TAR) is required.

1  "CANCEL" this order.

2  "PROCESS" this order. Treatment is for a pre-approved indication (chronic pylonephritis, osteomyelitis).

3  "PROCESS" this order. Requesting authorization (TAR) for treating pneumonia or a gastrointestinal infection.

| ACCUPRIL | | MC |

(Dose, Route, Frequency)

This drug is not on the Medi-CAL formulary. Prescribing this drug requires a pre-approved Treatment Authorization Request (TAR) to be on file.

1  "CANCEL" this order.

2  "PROCESS" this order. A pre-approved TAR is on file.

3  "PROCESS" this order. The patient is willing to incur drug expenses and knows that Medi-Cal will not pay reimbursement.

4  "SUBSTITUTE" with one of the following formulary drugs: "CAPTOPRIL", "ENALAPRIL", "FOSINOPRIL", "BENAZEPRIL"

Doe, John F   456753589   Blue Cr/MC        Poetry Systems

| NEW | DC | EDIT | LIST | OPEN |   Allergies   |   11/18/94   13:00
                                              NKA

INACTIVE PRESCRIPTIONS

MED REGIMEN              START       STOP

Lasix 40mg po bid        12/06/93    11/16/94
Digoxin 0.125mg po qd    03/14/92    11/16/94
Zantac 150mg po bid      04/19/91    06/25/93
Motrin 600mg po tid prn  07/30/91    06/25/93

ACTIVE PRESCRIPTIONS

1) Lasix 20mg po bid
2) KCl 20mEq po bid
3) Digoxin 0.25mg po qd
4) ASA 325mg po qd
5) Metamucil 1 tbsp bid
   prn constipation
6) Mylanta 30ml prn
7) Tyl #3 1-2tabs po q6h
   prn mild arm pain

INACTIVE PRESCRIPTIONS

PRESENT ACTIONS

FIGURE 67

Doe, John F  456753589  Blue Cr/MC  Poetry Systems

| NEW | DC | EDIT | LIST | OPEN | Allergies NKA | 11/18/94 | 13:00 |

INACTIVE PRESCRIPTIONS

| MED REGIMEN | START | STOP |
|---|---|---|
| Lasix 40mg po bid | 12/06/93 | 11/16/94 |
| Digoxin 0.125mg po qd | 03/14/92 | 11/16/94 |
| Zantac 150mg po bid | 04/19/91 | 06/25/93 |
| Motrin 600mg po tid prn | 07/30/91 | 06/25/93 |

ACTIVE PRESCRIPTIONS

1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

INACTIVE PRESCRIPTIONS

PRESENT ACTIONS

FIGURE 68

Doe, John F  456753589  Blue Cr/MC  Poetry Systems

| NEW | DC | EDIT | LIST | OPEN | | Allergies | 11/18/94 13:00 |
|---|---|---|---|---|---|---|---|
| | | | | | | NKA | |

INACTIVE PRESCRIPTIONS

Zantac   150mg po bid started: 04/19/91        J. Jones, MD
stopped: 06/25/93        W. March, MD
Dosing History:
04/19/91-06/25/93        150mg po bid

ACTIVE PRESCRIPTIONS

1. Lasix 20mg po bid
2. KCl 20mEq po bid
3. Digoxin 0.25mg po qd
4. ASA 325mg po qd
5. Metamucil 1 tbsp bid prn constipation
6. Mylanta 30ml prn
7. Tyl #3 1-2tabs po q6h prn mild arm pain

ANNOTATIONS

06/25/93 D/C Zantac. No further complaints of gastritis over the past 3 months. Rx for antacids prn.
02/03/93 Rx refill for Zantac from 12/29/92 never picked up. (Komoto's Pharmacy)
07/18/92 UCSF Drug Info: general incidence of HA & bloating is very low (<0.01%) for Zantac.
07/17/92 patient complaining of headache & bloating Q: Zantac related? Contacted UCSF Drug Information Service-answer pending.

INACTIVE PRESCRIPTIONS

PRESENT ACTIONS

FIGURE 69

Poetry Systems

Doe, John F   D231A   45675389

Allergies: NKA

[NEW] [DC] [EDIT] [LIST] [OPEN]

11/18/94   13:00

SCHEDULED meds
1. Lasix 20mg po bid
2. KCl 20mEq po bid
3. Digoxin 0.25mg qd

PRN medications
1. MS 2mg iv q4h prn
2. Tyl#3 1-2tabs po q4-6h prn

PRESENT ACTIONS
G-CSF 480mcg SQ QD

NEW ORDER ENTRY   [VIEW]

| G | - | C | S | F | | 4 | 8 | 0 | mcg | S | Q |

Please completed the following Drug Use Evaluation (DUE) information:

P & T approved indications:
1. myeloid malignacy - myelosuppressive regimen
2. non-myeloid malignacy - chemo regimen expected to result in ANC <500 for greater than 7 days
3. history of admissions for infections related to neutropenia from aplastic anemia, cyclical neutropenia, congenital neutropenia or myelodysplastic syndrome Other: [ ]

FIGURE 70

Doe, John F    D231A    4567535389

[NEW] [DC] [EDIT] [LIST] [OPEN]    Allergies SPECIFIED

PNEUMONIA,CHF    [5:9]    [ ]    [72]
DIAGNOSIS    AGE    HEIGHT    WEIGHT
                  (FT-IN)    (KGS)

DIAGNOSIS

| P | N | E | U | M | O | N | I | A |   |
|---|---|---|---|---|---|---|---|---|---|
| C | H | F |   |   |   |   |   |   |   |
|   |   |   |   |   |   |   |   |   |   |
|   |   |   |   |   |   |   |   |   |   |
|   |   |   |   |   |   |   |   |   |   |
|   |   |   |   |   |   |   |   |   |   |
|   |   |   |   |   |   |   |   |   |   |
|   |   |   |   |   |   |   |   |   |   |
|   |   |   |   |   |   |   |   |   |   |

Poetry Systems

11/18/94  13:00

SCHEDULED meds
① Lasix 20mg po bid
② KCl 20mEq po bid
③ Ampicillin 1gm iv q4h
④ Gentamicin 120mg iv q12h PRN medications
⑤ MS 2mg iv q4h prn
⑥ Tyl#3 1-2tabs po q4-6h prn
⑦ Phenergan 25mg im\iv q4-6h prn

PRESENT ACTIONS

FIGURE 71

INTERACTIVE MEDICATION ORDERING SYSTEM

BACKGROUND OF THE INVENTION

1. Technical Field

The present invention relates to a medication ordering system and more particularly to such a system that is both flexible and interactive and designed for rapid drug and prescription order entry and which has integrated into the system a resource and communication network providing the user with drug, patient, and prescribing information.

2. Discussion

The process of ordering or prescribing drugs is critically important in the practice of medicine. The choice of drugs requires the physician to draw upon a huge base of information regarding the patient's condition and medical history, knowledge of drugs and pharmacology, and clinical and therapeutic data. The physician's choice of drugs greatly influences the patient's clinical course as well as the overall cost of treatment.

Traditionally, physicians order drugs by writing an order in a chart for hospitalized patients or by writing a drug prescription on a prescription blank for outpatients. The physician typically relies on personal knowledge supplemented by available reference sources (e.g., books, journals, professional consultations, etc.) together with an in depth understanding of the patient's medical condition when formulating a therapeutic drug regimen.

Current computer systems show promise in improving the process of ordering and prescribing drugs. For example, a drug order or prescription could be entered directly into a computer and transmitted electronically thereby reducing the time from when the order is written to when it is received in the pharmacy. Numerous systems have been developed, that focus on order entry.

Generally, there are two types of hospital pharmacy computer systems. The first type is a "stand-alone" system. This is an independent pharmacy computer system that regulates all of the operational tasks such as medication dispensing, billing, inventory, etc. Typically, two separate hospital departments interface the "stand-alone" system. One department oversees patient admissions, transfers and discharges (ADT) and the other department accepts billing and financial transactions.

The second type of pharmacy computer system, the "total hospital system", is functionally similar to the "stand-alone" system but has been incorporated into a computer network that interconnects all departments of the hospital. Each department (e.g., laboratory, radiology, pharmacy, medical records) is accessible from computers located throughout the hospital.

With "stand-alone" systems medication order processing begins with the delivery of written or faxed orders to the pharmacy. Inefficiencies exist such as unnecessary paperwork and task duplication in the handling and delivery process. Orders are then entered into the computer by pharmacists or technicians. Furthermore, problems with medication orders are not quickly resolved because of delays involved from when the order was written, received by the pharmacy, and recognized by the pharmacist.

"Total hospital systems" attempt to improve the efficiency of the ordering process by transferring the responsibility for entering orders into the computer system to the prescriber (i.e., physicians). For example, these orders may include medications, laboratory tests, diets, etc. In these systems, the prescriber enters the orders directly from computer workstations. The result is a reduction in paperwork and task duplication. However, a number of problems remain. Computer order entry inefficiencies exist due to slow and cumbersome medication ordering pathways. For example, it is customary for pharmacy programs in "total hospital" systems as well as "stand-alone" systems to have rigid order entry pathways requiring numerous steps to accomplish simple tasks.

These pathways generally are of a fixed format entry style forcing the prescriber to follow specific steps (i.e., selecting in sequence the drug, dose, route and frequency) when entering medication orders. Different routes of administration for the same drug must be entered as separate orders. For example, an order for "Phenergan 25 mg PO/IM q6h prn" would require two separate order entries, one for selecting the oral (PO) tablet and the other for selecting the intramuscularly injected (IM) preparation. In addition, more complex orders (e.g., corticosteroid tapers) require extensive entry steps by the prescriber.

Furthermore, existing computerized medication order entry systems do not solve other inefficiencies in the order entry process. For example, relevant patient medication information is often not readily available to the prescriber in a complete, comprehensive and organized format. This includes lists of current and past medications, height, weight, and age, and information on drug allergies and adverse drug reactions. This information is important when making medication choices. Similarly, present systems often do not keep the prescriber informed of formulary information and drug availability, and of policies regarding hospital prescribing guidelines and restrictions. For example, prescribing information with respect to clinical practice guidelines, Medicaid restrictions, multi-disciplinary action plans (MAP's), clinical practice standards or clinical pathways all need to be communicated to the prescriber in an effective manner. Additional shortcomings in existing systems include the need for assistance in calculating drug doses using pharmacokinetic data, and the need for providing the prescriber with updated laboratory data relevant to the use and dosing of certain medications.

Because of these limitations in existing pharmacy computer systems, it would be desirable to provide a computerized medication order entry system that overcomes these inefficiencies and shortcomings. In particular, it would be desirable for such a system to be less rigid and easier to use. Ideally the system would mimic current and customary styles of medication ordering and adapt computerized pathways to process these orders. Furthermore, it would be desirable to provide a system that makes available to the prescriber a variety of information regarding the patient's medication history, allergies, drug interactions, recommended doses, etc. This desired system should alert the prescriber to drug interactions and adverse drug reactions to safeguard against untoward outcomes. This system would also communicate and enforce prescribing restrictions and guidelines as well as provide drug cost information. This desired system would also assist the prescriber in appropriate drug and dose selections based on individual patient information, pharmacokinetic evaluations and laboratory results.

SUMMARY OF THE INVENTION

The present invention is a system and method for ordering or prescribing medications for a patient. The system includes an improved process for allowing the prescriber to identify the patient using interactive software. The prescriber may interact with the system in various ways, that is with a keyboard and mouse, pen based entry, or voice entry. The system includes a database containing medical prescribing and drug information which is both general (e.g., pharmacology, dose recommendations, restrictions) and patient-specific (e.g., allergies, adverse drug reactions, medication history). The system also includes a program for accessing the database and displaying to the prescriber a list of active and inactive medications for the patient. The system accepts and processes medication orders and prescriptions for the patient from the prescriber which are typically comprised of drug product, dose, route of administration and frequency. In addition, the system communicates the medication order to the hospital pharmacy or the prescription to the outpatient/clinic/retail pharmacy. In the preferred embodiment, the system will accept medication orders or prescriptions entered in the computer in a random order entry format and then interpret and reformat the orders for processing.

In accordance with one aspect of the present invention, a process is provided which facilitates in selecting a patient and accessing all relevant health and medication information for that patient. The system also alerts the prescriber to potentially adverse situations that may result from an ordered or prescribed medication based on existing patient information in the database. For example, the system may warn the prescriber of a potential allergic reaction or drug interaction when a medication is ordered.

In accordance with another aspect of the invention, the system automatically determines product selection based on said descriptions (e.g., drug, dose, frequency, route of administration) and a means for communicating the order or prescription to the pharmacy. The system includes an interface for creating and storing information relating to predetermined situations such as ordering non-formulary drugs, prescribing restrictions for specific drugs, unrecognized or unavailable drug entries, questionable dose entries, potential drug interactions and defined order sets. The system automatically displays a configuration specific message to the user when said medication order or prescription represents the occurrence of one of these predetermined situations. An interface is provided to define these pre-determined situations, and to create the messages. In addition to messages, through this interface the user can create predetermined sets of orders that are triggered to appear when specific mnemonic codes are entered.

In accordance with another aspect of the present invention a process is provided to evaluate drug use and dosage based on available laboratory and pharmacokinetic information.

BRIEF DESCRIPTION OF THE DRAWINGS

The various advantages of the present invention will become apparent to one skilled in the art by reading the following specification and by reference to the following drawings.

It should be noted that, the specific format, gridmarks within, and visual style of fields in the referenced screens may vary to accommodate the preferred implementation of the present invention by the user.

FIG. 2 shows how the user identification code is entered when the user signs onto the system whereby the system is restricted to authorized users only.

FIGS. 4 and 5 depict the process of selecting a patient by name in accordance with the present invention.

FIGS. 6 and 7 depict the process of selecting a patient by unit and bed number in accordance with the present invention.

FIG. 8 depicts the process of selecting a patient by medical record number in accordance with the present invention.

FIG. 9 is a patient profile screen for physicians in accordance with the present invention.

FIG. 10 is a patient profile screen for non-physicians in accordance with the present invention.

FIG. 11 is a free format screen for entering orders, messages or annotations in accordance with the present invention.

FIG. 12 is an order authorization screen in accordance with the present invention.

FIG. 13 is an allergy window indicating the nature of a specified allergy in accordance with the present invention.

FIG. 14 is a new order entry screen in accordance with the present invention.

FIG. 15 is a medication view window in accordance with the present invention.

FIG. 16 depicts the process of selecting a medication from the view window in accordance with the present invention.

FIG. 17 is an example of an order completed for a selected medication in accordance with the present invention.

FIG. 18 depicts a medication selected from the view window in accordance with the present invention.

FIG. 19 depicts a new medication selected from the view window in accordance with the present invention.

FIG. 20 depicts a new medication order completed in accordance with the present invention.

FIG. 21 is the non-formulary drug message screen.

FIG. 22 depicts the simultaneous functions which may be performed by the user utilizing the present invention.

FIG. 23 depicts the therapeutic interchange message screen of the present invention.

FIG. 24 depicts an order for multiple routes of administration utilizing the present invention.

FIG. 25 is a screen for initiating a medication taper order in accordance with the present invention.

FIG. 26 is the resulting screen for medication taper order which follows the screen depicted in FIG. 25.

FIG. 27 is a screen for facilitating the order of total parenteral nutrition.

FIG. 29 is a screen depicting the process of discontinuing an order in accordance with present invention.

FIG. 30 depicts the process of viewing current or past medication orders utilizing the present invention.

FIG. 31 depicts a view screen for past medications in accordance with the present invention.

FIG. 32 is a screen containing a message for possible drug allergy in accordance with the present invention.

FIG. 33 is a message screen for dose availability produced by the present invention.

FIG. 34 is a message screen for potential drug interaction produced by the present invention.

FIG. 35 is a message screen depicting a pharmacokinetics recommendation made by the present invention.

FIG. 36 is a message screen for unrecognized medication name in accordance with the present invention.

FIG. 37 depicts the use of the scrolling bar for viewing medication lists in accordance with the present invention.

FIG. 38 depicts the full viewing of present actions window in accordance with the present invention.

FIG. 39 depicts all of the orders being displayed as present actions utilizing the present invention.

FIG. 40 depicts the screen for selecting take home medications using the present invention.

FIG. 41 depicts the screen for ordering a medication order set in accordance with the present invention.

FIG. 42 depicts the displaying of a medication order set utilizing the present invention.

FIG. 43 illustrates the selecting of a medication order to edit utilizing the present invention.

FIG. 44 depicts the editing of the medication order utilizing the present invention.

FIG. 45 depicts the process of completing the medication order edit utilizing the present invention.

FIG. 46 is an illustration of a message indicating prescribing restrictions generated by the present invention.

FIG. 47 illustrates the process of accessing the drug information database.

FIG. 48 depicts a display from the drug information database utilizing the present invention.

FIGS. 49A–L are a series of diagrams depicting system features, including the process steps performed by the order reformatter and interpreter in accordance with the present invention.

FIG. 50 is a screen illustrating the use of updated laboratory information in accordance with the present invention.

FIG. 51 depicts the opening screen for the outpatient/clinic program utilizing the present invention.

FIG. 52 depicts examples of patient specific messages and the steps taken to open a detailed drug file utilizing the present invention.

FIG. 53 depicts the prescribing of a non-formulary medication on the new prescription entry screen utilizing the present invention.

FIG. 54 depicts the non-formulary message window utilizing the present invention.

FIG. 55 depicts a detailed drug profile screen illustrating the annotations window utilizing the present invention.

FIG. 56 depicts an example of prescribing a non-formulary drug utilizing the present invention.

FIG. 57 depicts the non-formulary message screen with selection that include substitute alternatives utilizing the present invention.

FIG. 58 depicts the new prescription entry screen with the non-formulary drug replaced by the substitute alternative utilizing the present invention.

FIG. 59 depicts writing an annotation to a prescription file utilizing the present invention.

FIG. 60 depicts the new prescription entry screen utilizing the present invention.

FIG. 61 depicts the screen for selecting a drug file to record an annotation utilizing the present invention.

FIG. 62 depicts the process of writing a drug file annotation utilizing the present invention.

FIG. 63 depicts the process of viewing a detailed drug file including starting date, dosing history, ordering physician, and annotations utilizing the present invention.

FIG. 65 depicts the construction of a message utilizing the present invention.

FIG. 66 depicts the construction of a message including substitute drug alternatives utilizing the present invention.

FIG. 67 depicts the inactive prescriptions opening window.

FIG. 68 depicts the screen for selecting an inactive file to review.

FIG. 69 depicts the viewing screen of an inactive prescription file.

FIG. 70 depicts the drug use evaluation screen.

FIG. 71 depicts the diagnosis window.

DETAILED DESCRIPTION OF THE PREFERRED EMBODIMENTS

The pharmacy of the present invention has two primary embodiments. The first is an inpatient pharmacy system designed as an interface to preexisting hospital pharmacy systems. The second is a pharmacy system to be used in outpatient and clinic settings. In both versions the software is designed to accommodate customary medication ordering styles and practices in lieu of rigid fixed format entry (i.e., selecting in sequence the drug, dose, route, frequency). That is, the pharmacy system of the present invention will recognize random order entry format (e.g., selecting in no particular sequence the dose, drug, frequency, route, etc.) to facilitate user friendliness. The pharmacy system incorporates multiple styles of order entry utilizing input commands by either voice, pen, mouse and keyboard or any combination of more than one of these command styles (e.g., voice and pen). The descriptions for each command style are not provided in the subsequent text for every process, however, this does not imply a restriction to the user. The system also provides an interactive screen display designed for quick access to patients and rapid ordering with a minimal number of steps. Further, the system displays complete and current medication lists on the order entry screen. The prescriber is freed from many tasks normally associated with the medication order process such as product formulation selection (i.e., selection of tablet, suspension, injection, etc.), billing qualifiers (units to charge per dose), and drug administration timing (for nurse's medication administration charting). These tasks are accomplished by a series of programs, invisible to the user, which provide functions such as automatic product selection based on route of administration, as well as product compounding and formulation (infusion solutions, syringes, topical preparations, irrigations, etc.).

Furthermore, the pharmacy system of the present invention incorporates immediate bi-directional communication to relay drug and cost information, drug availability and the need for order clarification. The system also responds to "safety net" issues such as assistance with medication dosing and alerts for drug interactions, potential allergies, and adverse drug reactions. The message environment also serves to regulate specific institutional prescribing practices and guidelines, convey formulary information, and collect data for drug usage evaluation.

Color highlighting and shading will be utilized in all functional aspects of the Poetry System 10. For example, command buttons, windows, window titles, selected medications will be color highlighted as well as process selections (e.g., the RENEW button highlights in the same color as the medications to be renewed or the DC button highlights in the same color as the selected medications to be discontinued).

Figure 1:
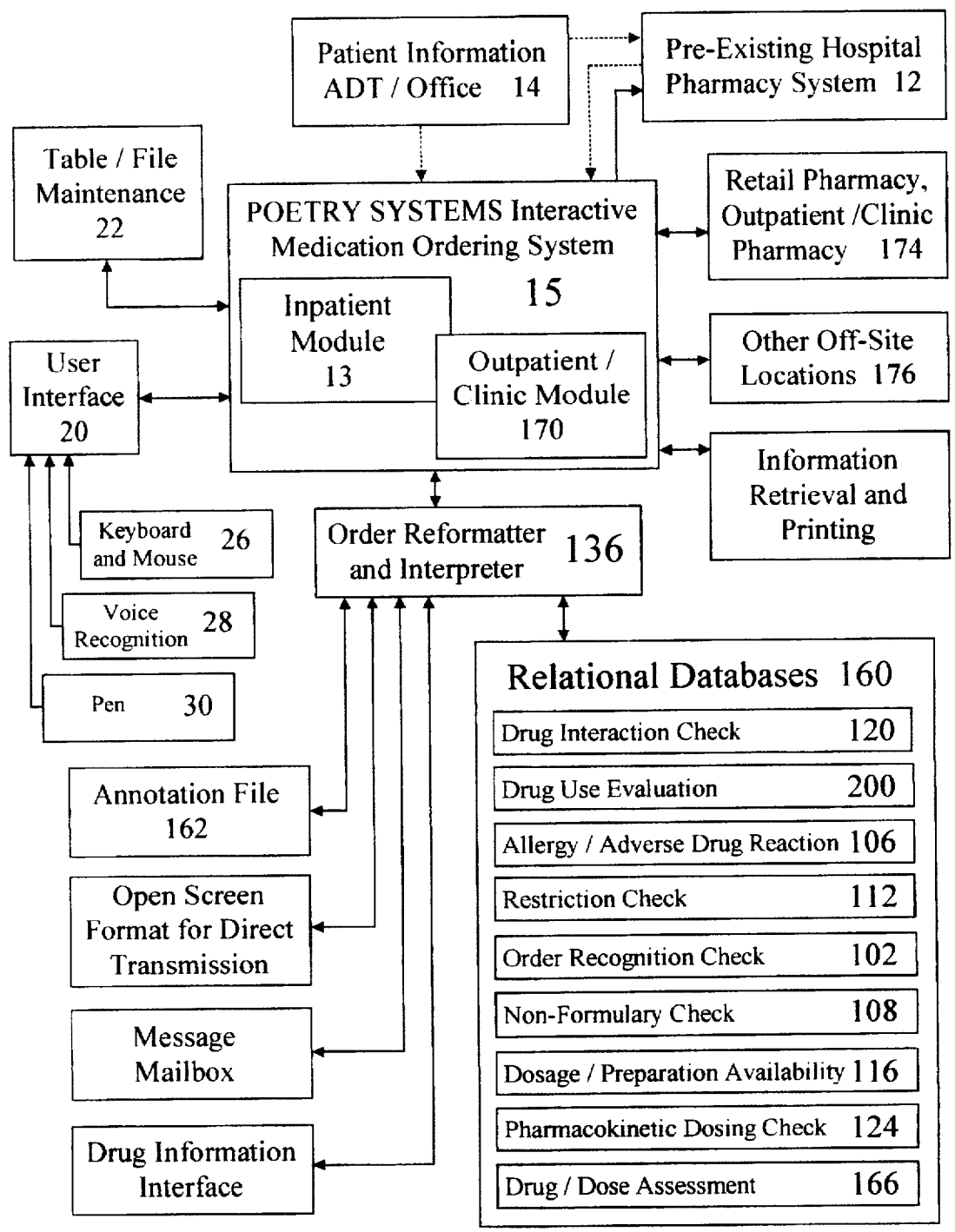
FIG. 1 is an overall system diagram of the Poetry Computerized Pharmacy System of the present invention adapted for use in accordance with a first embodiment of the present invention.

Referring now to FIG. 1, an interactive medication ordering system 10 in accordance with the present invention is shown. In one embodiment the system 10 is configured with an inpatient module 13 which permits the system to interface with a preexisting hospital pharmacy system 12. Patient admission, discharge and transfer (ADT) information can flow from the ADT unit interface 14 directly to the inpatient module 13 or via the pre-existing hospital pharmacy system 12. ADT data includes patient name, medical record number, account numbers, address, date of birth, allergies, physicians, insurance information, clinic information, nursing station and bed number. In addition, (or alternatively) the system 10 can be configured with an outpatient/clinic module 170 which permits the system 10 to interface with a retail pharmacy or outpatient/clinic pharmacy 174 as described in more detail below. A preferred embodiment of the interactive medication ordering system will also be referred to as the POETRY SYSTEMS™ interactive medication ordering system 15.

The inpatient module 13 performs all of the primary processing functions represented by the order reformatter and interpreter 136. Connected to the inpatient module 13 is a user interface 20 which accepts input via keyboard and mouse 26, voice recognition 28 or pen interface 30 or any combination of command input style.

Referring now to FIG. 2, a representative sign-on opening screen 32 is shown that would appear at the user interface 20 in accordance with the present invention. The prescriber user, generally a physician, will initially be presented with the sign-on opening screen 32. The physician will sign on to the system with a representative identification code and signature according to the on-screen instructions. From this screen the user can access either the inpatient 13 or outpatient/clinic 170 module. Access to information and functional features of the Poetry System 10 will be limited to authorized users only.

Figure 3:
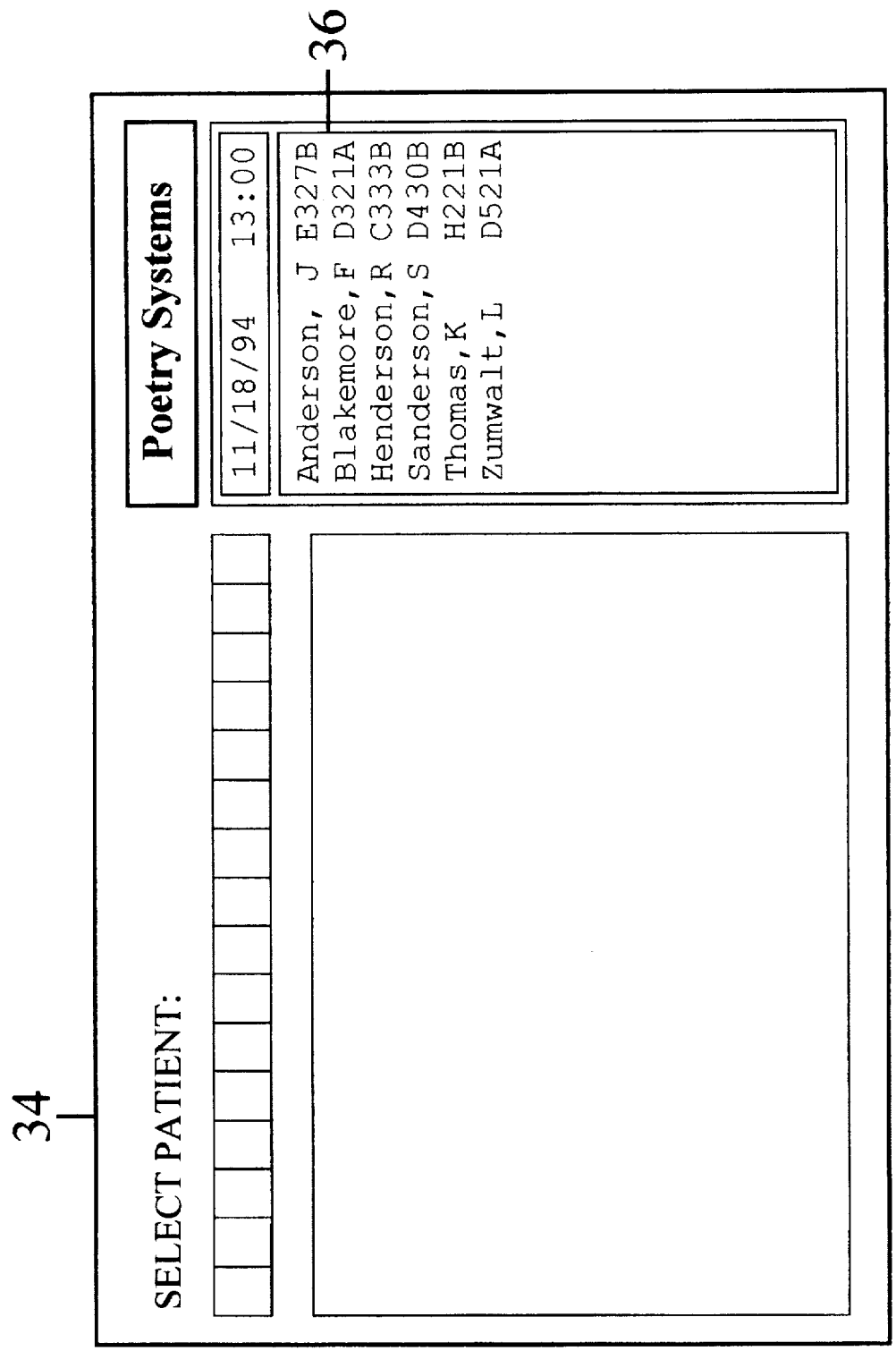
FIG. 3 is the patient selection screen in accordance with the present invention.

In response, the system 10 will display a list 36 of that physician's patients with their room numbers as shown in the patient select screen 34, in FIG. 3. The physician has a number of alternatives at this point. The physician may choose to select one of the patient's names with the pen or mouse and the system will directly display that patient's medication profile. Alternatively, if the desired patient name does not appear on that list, the physician may begin writing, typing, or spelling (using the voice recognition unit 28) a patient's last name, medical record number, nursing unit or bed number. If the physician begins writing, typing, or spelling the last name of the patient, a list of all patients beginning with the written, typed, or spoken letters are displayed on the screen. For example, if the physician enters the letter D as shown in the screen 35, in FIG. 4, a list 38 of all current in-patients having a last name beginning with the letter D is presented. If the physician enters the letters D and O the screen 40, in FIG. 5, will present a list 42 of patients whose last name begins with the letters "DO". Writing, typing, or speaking additional letters will further refine the list of patient selections. Alternatively, the physician may pronounce the patient's last name and if recognized, all patients with that spoken last name will be listed on the screen.

Alternatively, the physician can write, type, or speak the patient's nursing unit. For example, "D2" will produce a list 44 of all patients in units beginning with the symbols D2 as shown in the screen 46, in FIG. 6. In addition, the physician may write, type, or speak the patient's bed number which will generate the name of the patient with that specific bed number as shown in screen 48, in FIG. 7. Lastly, the patient can be selected by medical record number as shown in the screen 50, in FIG. 8. In each case, as shown in FIG. 8, a partial entry will produce a list of all patients having that partial entry in common. Writing, typing or speaking additional numbers will further refine the list of patient selections.

The physician can select a patient's name and the system will display that patient's medication profile as shown in screen 54, in FIG. 9. The patient profile screen 54 includes the patient's name, bed number, medical record number, message mailbox 56, selection options 58, "orders to countersign/renew" box 60, list of patient's current schedule 62 and PRN medications 64. At this point the physician may review the messages in the message mailbox 56, orders to countersign or renew 60 or continue to other functions 58.

It should be noted that non-physicians such as nurses and pharmacists can also sign on to the system with a representative identification code and signature as shown in FIG. 2. However, upon sign on no initial list of patients will be provided as it is for physicians. The non-physician user can then proceed to select patients as described above in connection with FIGS. 4–8 to reach the patient profile screen for non-physicians 66, in FIG. 10. This profile screen is similar to the one for physicians except it only includes messages and orders to renew box 69.

With respect to the message screen 56 and 69, in FIGS. 9 and 10, respectively, messages pertaining to the selected patient are displayed in the messages mailbox. All users can read and then erase messages by a.) using the pen 30 or mouse 26 to select the erase box and then the numbered box in front of each message; or, b.) speaking 28 the erase command and then the message number. Messages that are not erased will be retained in the system for a period of time selected by the hospital administration and then automatically deleted. Within the retention period, messages not deleted will be displayed in the message mailbox each time a user signs on to the system and selects the patient.

All users have the ability to enter orders and information on a free format screen 70 in FIG. 11. The user accesses this screen by using the pen or mouse to select the OPEN button 68, or by speaking the "open" command. In response, a free format screen 70 will appear for the user to select the order 71, message 73, or annotation 75 button. If the message 73 button is selected, the user can begin to write or type a message specific to that patient. After completing the message the user selects "POETRY SYSTEMS" 72 with the pen or mouse and the free format screen will close and the written message will be place in the message mailbox for that patient. Newly created messages will be displayed in the message window (56 and 69) on the patient profile screen (9 and 10). If the order 71 button is selected, the written or typed order is automatically transmitted and printed in the pharmacy when the user selects "POETRY SYSTEMS" 72. If the annotation 75 button is selected, the written or typed annotation is entered into the selected drug file upon completion. A more detailed description of the annotation procedure is described in a later section.

Non-physicians (e.g., nurses, pharmacists, respiratory therapists) are not allowed to prescribe or order medications unless taking verbal or telephone orders from physicians. The physician must countersign verbal telephone orders within 24 hours in the countersign/renew box 60, in FIG. 9. For medication orders that require countersignature, in FIG. 9, the orders are listed with the medication and its directions, the date and time that the order was entered, the name of the clinician who entered the order followed by the ordering physician's highlighted name. The physician may use the pen or mouse to select the highlighted name at the end of the order so that order is immediately filed with that physician's electronic signature and disappears from the screen. A physician may countersign another physician's orders (when on-call or covering for that physician).

Orders requiring renewal are noted by the highlighted "renew" 60 and 69 (See FIG. 9 and 10) in the heading along with highlighted orders in the current scheduled and PRN medication lists. To renew an order, the user selects the highlighted renew word 60 and 69 and then the highlighted medication order from the current scheduled and/or PRN medication boxes, or the user can pronounce the renew command and then the number of the medication being renewed. The renewed medications are then listed in the "present actions" box 74, in FIG. 9 for processing along with other new actions until the user completes the order session by selecting "POETRY SYSTEMS" 72, in FIG. 11, with the pen or mouse. The renewed order and other medication orders will be printed in the pharmacy and at the patient's nursing station. When the non-physician is renewing an order, the "order authorized by" box must be completed before the order for renewal is processed. See order authorization screen 80, in FIG. 12. This process is consistent with any order entered by non-physicians.

As shown in FIG. 9, the user is always presented with windows displaying the patient's current scheduled 62 and PRN 64 (as needed) medications as well as a "present actions" box 74. These sliding windows are of fixed width and limit window bar movement to a single axis. The three title bars cannot be hidden from view and retain their relative positions. Selection of the title bar maximizes the display of the contents of the selected window. Accommodating the display of the completed contents of the scheduled meds 62 window will take precedence over displaying the completed contents of the PRN 64 window on the initial patient profile screen (screen 54 for physicians and 66 for non-physicians).

Figure 38:
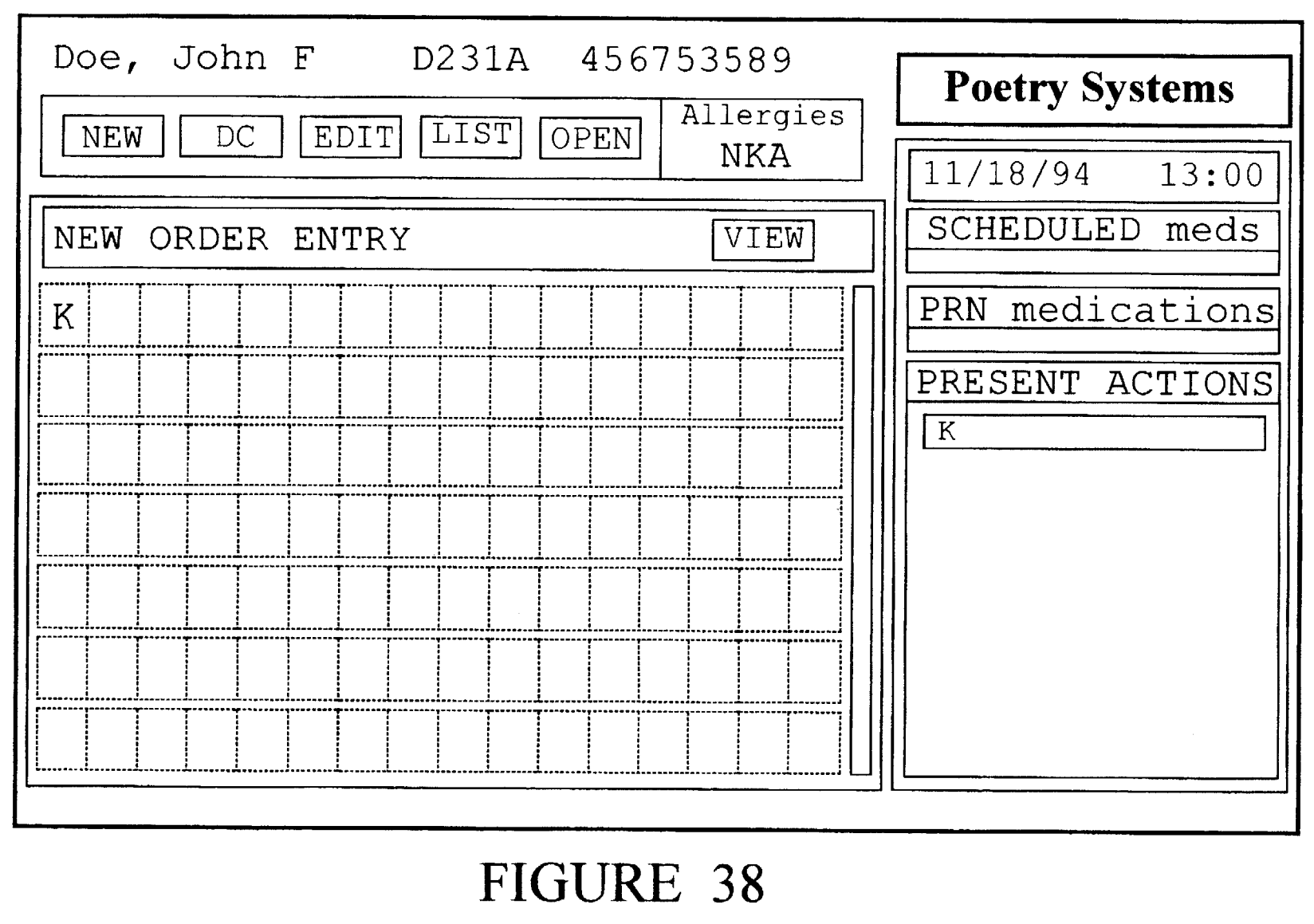

The size of each box will change to accommodate the listing of all qualified medication orders. If the boxes cannot display all the current medication orders, the boxes will have vertical scroll bars to accommodate viewing of all the orders (See FIG. 37). All actions such as new order entry, renewing orders, editing orders, discontinuing orders and adding, revising, or deleting allergy information by the user will be listed in the "present actions" box (See FIG. 39). The scheduled and PRN boxes will "slide" to allow viewing of present actions by the user (See FIG. 38). If review of the patient's scheduled or PRN medication orders is needed during this time, the user uses the pen or mouse to select either the "SCHEDULED meds" or "PRN medication" headings to enlarge those boxes. The present actions box will then slide to allow the "SCHEDULED meds" or "PRN medications" boxes to open again. To return to or to enlarge the present actions box again the user selects the present actions heading or continues writing orders for the patient.

An allergies box 76, in FIG. 9, will display a number of possible literals (i.e., NKA, specified, unspecified). "NKA" indicates that the patient has no known allergies, "specified" indicates that allergies have been noted, and "unspecified" indicates that allergy information has not been collected. The user selects the allergies box with the pen to open the allergies window which lists all allergies along with the adverse reactions. To delete an allergy, the user lines through or highlights and deletes the allergy. To add an allergy, the user writes or types the allergy with the adverse reaction on the next available blank line. For example, referring to FIG. 13 the allergy window 78 is shown. Entries may be made by voice or other means to indicate medication allergies and adverse reactions. When the user opens the allergy window (shown in FIG. 13 for a case where there are specified allergies), the patients height, weight, age and admitting diagnosis are also displayed with the allergies. If the patient's height and/or weight have not been previously noted, the user can write, or type the height and/or weight into the blank space provided. Admitting diagnosis and age are collected from the ADT interface 14 (See FIG. 1). Selecting the diagnosis box will open the diagnosis window to display more comprehensive diagnosis information (See FIG. 71). Additional information can also be entered.

Referring to FIG. 14 the new order entry screen 82 is shown. The user enters new medication orders for the selected patient by using the pen or mouse to select the "new" button 84 on the screen. Alternatively, the user can speak the "new" command. The screen changes to display a "new order entry" subheading with the word "view" in a box on the same line. The user can begin writing or typing the letters of the medication name, speaking the alphabetic characters or speaking the medication name or combination of the above. The user can continue writing, typing or speaking the dosage, route, frequency and duration of the order or can choose to view the medication formulary for the written, typed, or spoken medication. By using the pen or mouse to select the "VIEW" box 85 or speaking the "VIEW" command, the system allows the user to view the availability of the drug, its various strengths, dosage forms and costs. This information is shown in the medication view window 86, in FIG. 15. The user selects the drug and dose with the pen or mouse, or speaks the drug name and dose, and the screen changes to list the drug and dose in the order entry screen shown in FIG. 16. Completion of the order proceeds with route of administration, frequency and duration (in any sequence) as shown in the order entry screen 90, in FIG. 17. If the user selects the drug line in the "VIEW" window with the unspecified dose, the user must also include the dose along with route of administration, frequency and duration to complete the order.

The user can also scroll backward or forward to view the entire drug formulary from the original "VIEW" drug selection. For example, if "cefazolin" is selected for initial viewing the user can scroll back through the list to view "bumetanide" or scroll forward to view "doxycycline".

In the "VIEW" window the user can scroll and select any drug. The order entry screen will change to reflect the new selection. For example, an antibiotic, cefazolin, is entered on the order entry screen 88, in FIG. 16, and the "VIEW" function is selected. From the "VIEW" window 92, in FIG. 18, a new antibiotic, ceftazidime, is selected and when the view window is closed this new drug appears in the order entry box in screen 94, in FIG. 19. The user completes the order as shown in screen 96 in FIG. 20. Note the "PRESENT ACTIONS" box 74 reflected all of the selected changes made throughout the ordering process for this individual order (See FIGS. 18–20).

The user can enter more than one new medication order or perform other functions such as editing an order, discontinuing an order or adding, revising or deleting allergy information before completing the order session by selecting "POETRY SYSTEMS" 72 (See FIG. 11) with the pen or mouse. The screen 98, in FIG. 22, illustrates a multiple order actions session.

Once an order is entered the order reformatter and interpreter 136, in FIG. 1, will proceed through a series of steps to check for a number of conditions.

One such check is for the recognition of a medication being ordered as shown in screen 100, in FIG. 36. In this example, an unrecognized drug name message will be displayed and the prescriber will be given a list of similar recognizable alternatives. Alternatively, the prescriber may send the order as written. Furthermore, the order reformatter and interpreter 136, in FIG. 1, will check for recognition of the dose, route of administration, frequency and duration. All of these recognition tasks are performed by a order recognition function 102, in FIG. 1.

An additional check is for possible allergies or adverse drug reactions as illustrated on screen 104, in FIG. 32, by function 106, in FIG. 1.

The non-formulary function 108, in FIG. 1, will check the order to determine if it is formulary or non-formulary as illustrated in the non-formulary drug message screen 110, in FIG. 21.

A number of different formularies will be categorized in this database including lists for the hospital, managed care providers, insurance plans and pharmacy benefits managers. In addition, within each formulary, drugs can be selected for "preferred" or "most appropriate" status. Messages can be constructed to relay this information to the user. The existence of any prescribing restrictions as set forth by the hospital P and T (Pharmacy and Therapeutics) committee is performed by the restriction function 112, in FIG. 1, as illustrated in screen 114, in FIG. 46.

Dosage availability is determined by the dosage availability function 116, FIG. 1, as illustrated by screen 118, in FIG. 33.

The system will also check for drug interactions in the drug interactions function 120, in FIG. 1, shown in the drug interaction screen 122, in FIG. 34.

The drug/dose assessment function 166, in FIG. 1, will check for acceptable dose ranges for medications.

The system can also perform pharmacokinetic dosage calculations in function 124, FIG. 1, as shown in screen 120, in FIG. 35.

The system will also check the Drug Use Evaluation (DUE) database 200, in FIG. 1. Ordering drugs included in this database will result in specific messages to the user (See FIG. 70). Notations from these orders will be included in the annotations section of the corresponding medication files.

If a non-formulary medication is prescribed, the user will be given a series of options as shown in screen 110, in FIG. 21, as well as in screen 128, in FIG. 23. That is, the user will be given the option of substituting the non-formulary medication with a therapeutically equivalent medication that is on the formulary, request that the non-formulary medication be specially ordered, or allow the patient to take his or her own medication supply from home. In some cases, the therapeutic interchange message screen 128, in FIG. 23, will be presented for non-formulary orders along with a message explaining the hospital-approved substitution policy.

If a medication is administered via a naso-gastric tube, the system will check for the recommended dosage range and frequency via this route of administration. This system will automatically choose the liquid dosage form of the medication if available. This will be performed by the dosage function 116, in FIG. 1. The system will allow an order for multiple routes for administration to be entered as a single order as shown by screen 130, in FIG. 24. For example, "IV/PO" (intravenous/oral administration) or "IV/IM/PO/PR" (intravenous/intramuscular/oral/rectal) type orders can all be entered as one order.

In addition, the system provides for easy entry of "tapering" medication type orders as shown in screens 132 and 134, in FIGS. 25 and 26, respectively. Tapering is the process of decreasing the dose of a medication over an extended period of time as opposed to abruptly stopping the medication. This is usually done with drugs that can cause adverse effects to the patient if the drug is abruptly withdrawn. As shown in FIG. 25, the user may write, type or speak the "TAPER" command in this case "Decadron taper". This will cause the screen to change to screen 134, in FIG. 26, which allows the user to specify the start and stop date along with dose and route. The user will not have to write a separate orders for the IV and PO routes of administration if the medication is to be given either IV or PO (IV/PO).

The system also recognizes common abbreviations or slang terms as well as orders entered in a random format (i.e., No specific sequence for drug, dose, route of administration, or frequency required). These functions are performed by the order reformatter and interpreter 136, in FIG. 1. The entering of these elements (drug, dose, route of administration and frequency) can be in any order or logical combination. In addition, any or all of the elements can be entered by keyboard or mouse 26, voice entry 28, or pen entry 30 or by a combination of these. For example, the user may type the drug name with the keyboard, speak the dosage, write the route of administration with the pen, and speak the frequency. The hospital pharmacy system 10 of the present invention will recognize these various order subsets (e.g., drug, dose, route and frequency) and will translate the information to the interfaced pharmacy system 12, in FIG. 1. For various drugs, there will be a "default" route of administration. If the route is not specified by the user, the system will "default" the route based on the medication and dosage ordered. Orders can also include qualifiers such as order instructions (e.g., "limit to 8 tablets per day") or administration parameters (e.g., "hold antihypertensive medications (s) if heart rate is less than 70 or the systolic blood pressure is less than 130").

Medications can be ordered for non-standard administration frequencies. For example, "QMWF" (i.e., every Monday, Wednesday and Friday) or "Q3 days PRN" (i.e., every three days as needed). Orders can be for single dose drug administration using various "urgency qualifiers" (e.g., now, STAT, ASAP). The system will also recognize orders for medications to be administered at a future time or date.

Another ordering format is "bolus and intermittent injection". This is for medications that are given as a one time bolus (or loading dose) with subsequent "maintenance" doses at scheduled intervals. The system will schedule the loading dose with the subsequent maintenance doses to start at the specified interval. Alternatively, the system may accept medication orders that are given as a one time bolus or loading dose with a subsequent continuous I.V. infusion (drip) or recognize and accept orders for medications to be given by continuous infusion without a loading dose.

The user also has the option of using pre-defined medication order sets. An order set is a standard medication list that a physician uses in specific circumstances. For example, an order set used by obstetricians for post-partum women may include orders for stool softeners, anti-nausea medications and analgesics. The user can create an order set triggered by a mnemonic code to recall a series of "preprinted" medication orders as illustrated by screen 136, in FIG. 41. The pre-defined orders are automatically listed in the present actions box and the contents of the order set will be displayed on screen 138, in FIG. 42. The user can exclude any orders from the displayed order set by lining through those specific orders with the pen or by highlighting and deleting those orders with the mouse and keyboard. As the orders are lined out or deleted, the orders disappear from the writing area on screen 82, in FIG. 14, as well as from the present actions box 74. The user also has the option of changing any of the pre-defined orders in the order set displayed on the screen before final entry. As the order set orders are changed in the writing area on the screen 82, the orders are also changed in the present actions box 74. Sliding scale orders comprise different doses of the same medication and administration depends on laboratory test results. Sliding scale orders can be a version of a pre-defined medication order set. The user has the ability to accept the order set as it is defined and displayed or change any part of the sliding scale order. PCA or Patient Controlled Analgesia orders are another version of a pre-defined medication order set. The system will recognize the letters PCA followed by the name of the narcotic ordered. The system can be tailored to meet the ordering format outlined by the hospital's P and T (Pharmacy and Therapeutics) committee.

Total parenteral nutrition (TPN) or peripheral parenteral nutrition (PPN) orders are another version of a pre-defined order set. When the user writes TPN or PPN, the screen automatically changes to the parenteral nutrition ordering format as illustrated in screen 140, in FIG. 27.

Figure 28:
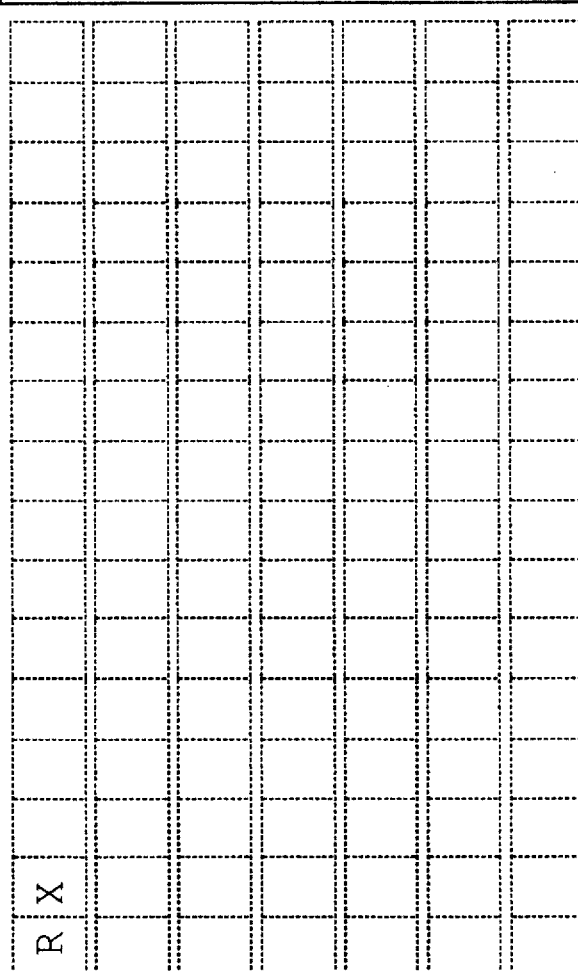
FIG. 28 is a screen depicting the initiation of an order for take home medications in accordance with the present invention.
Figure 49A:
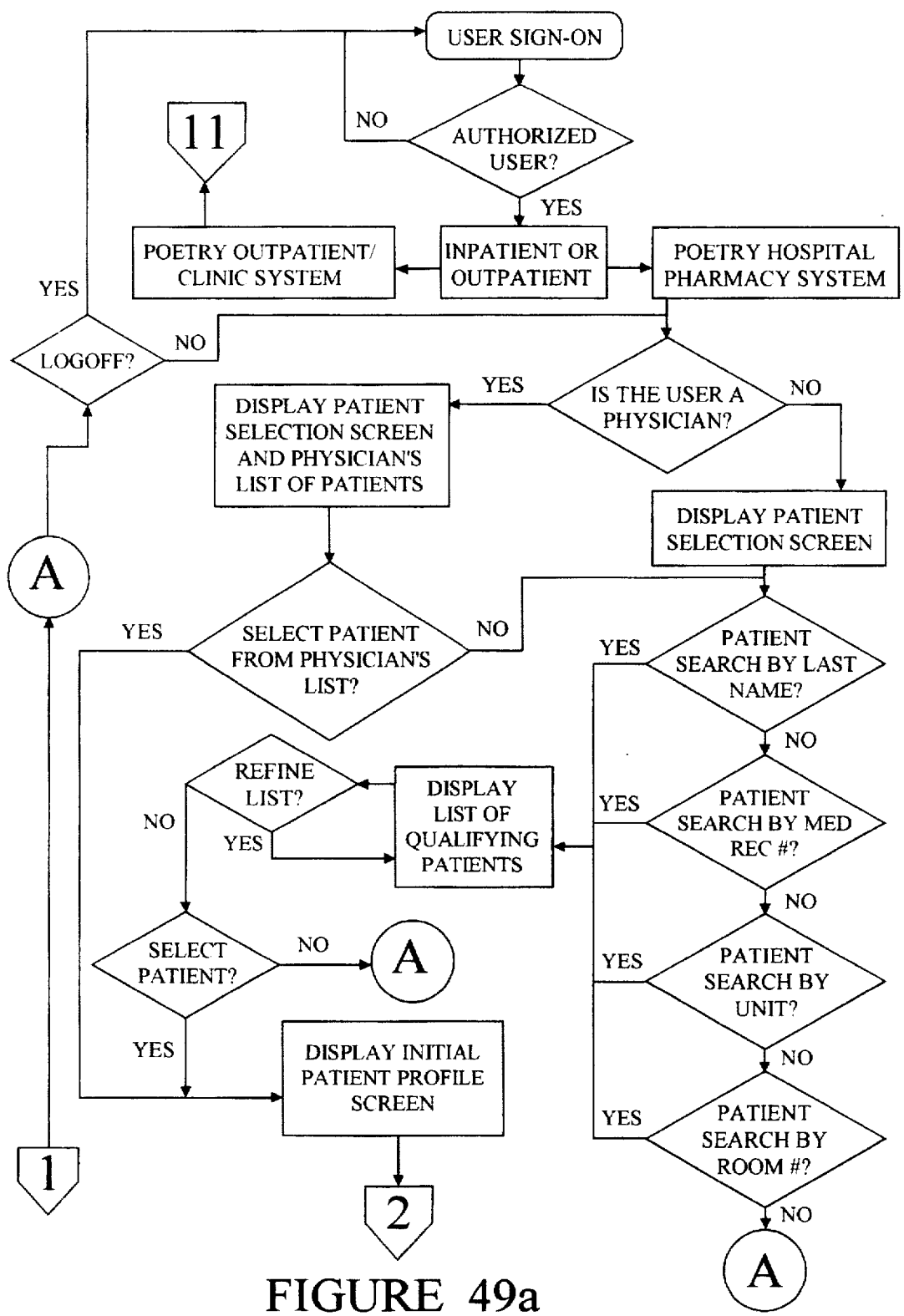
Figure 49B:
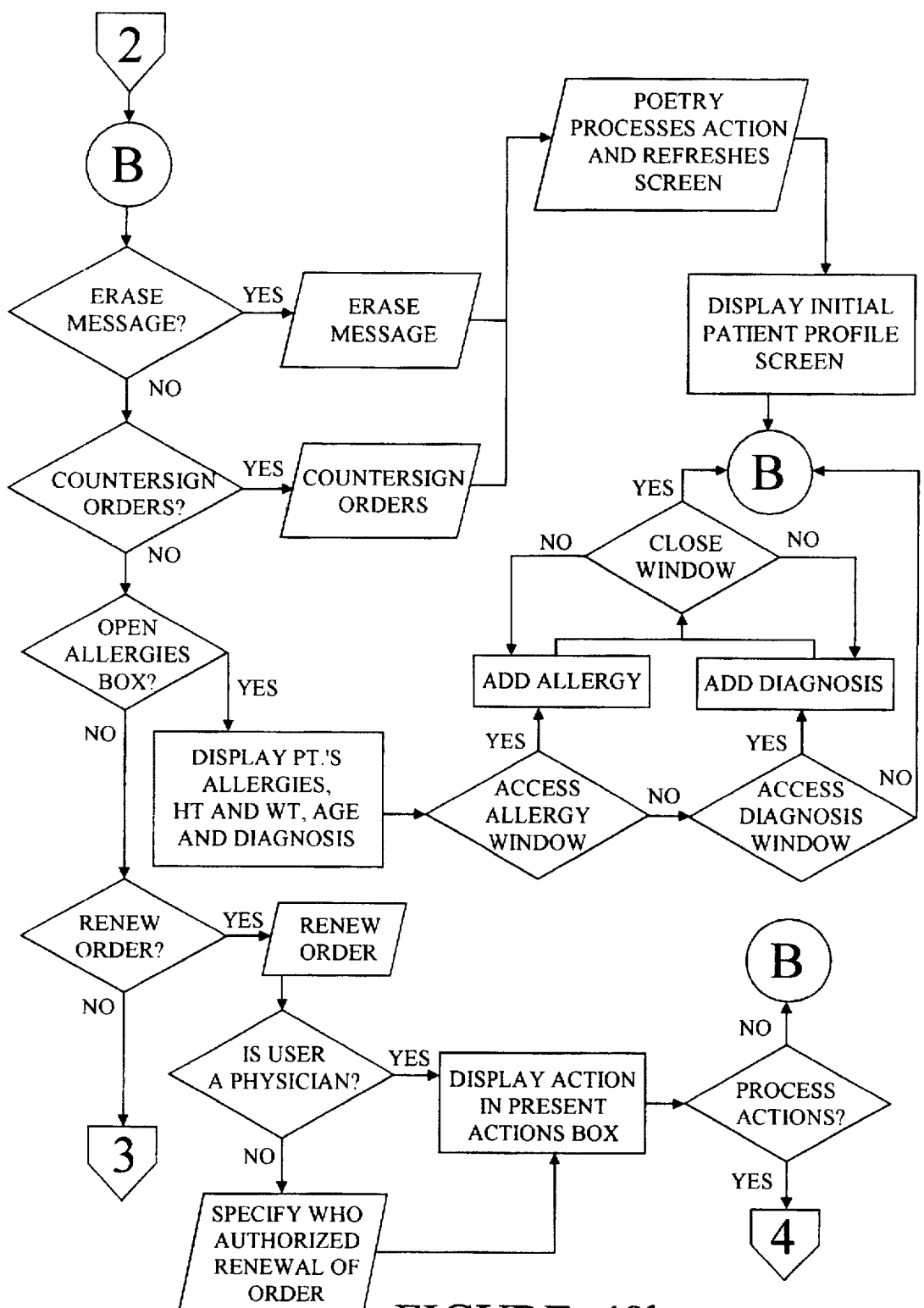
Figure 49C:
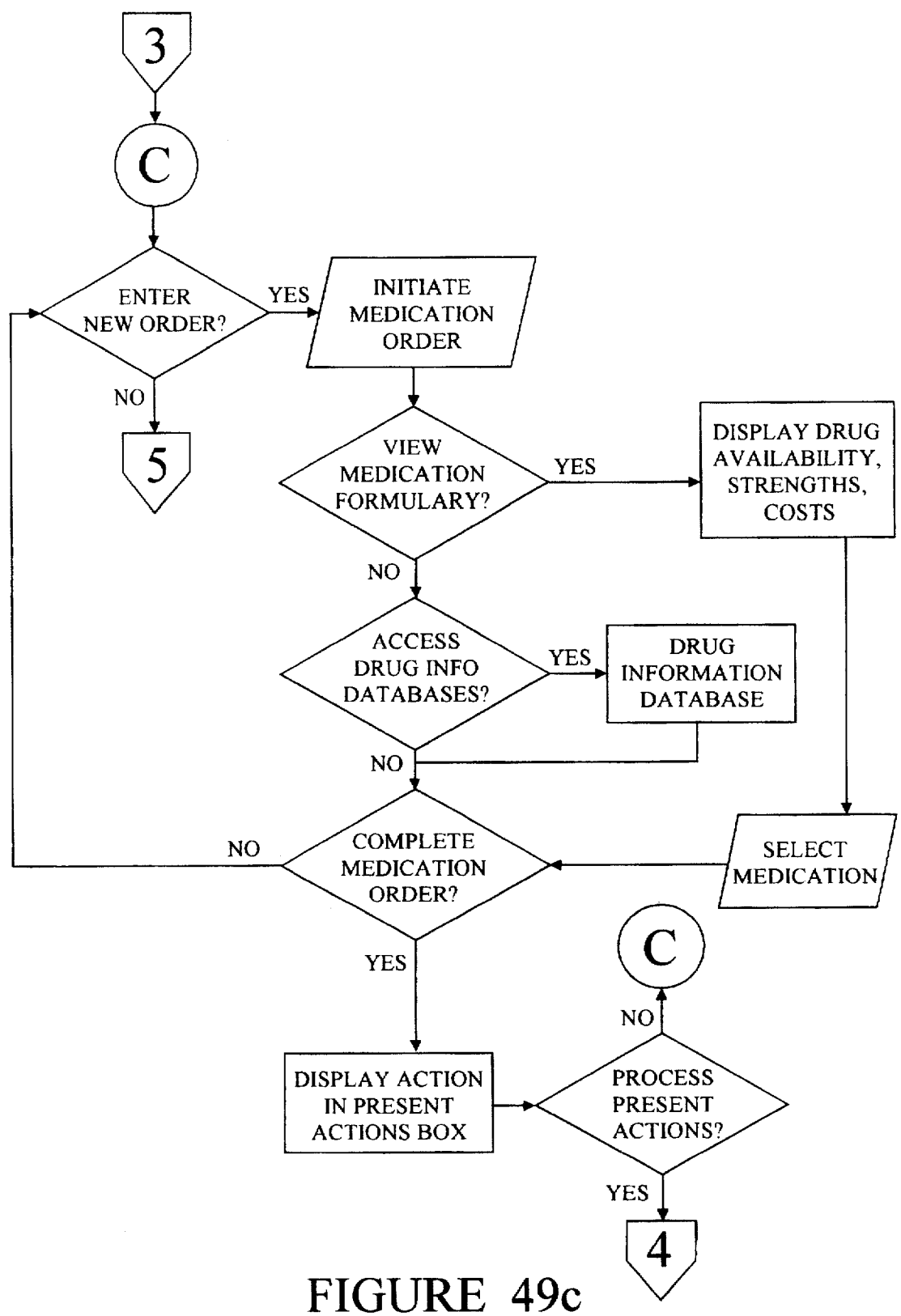
Figure 49D:
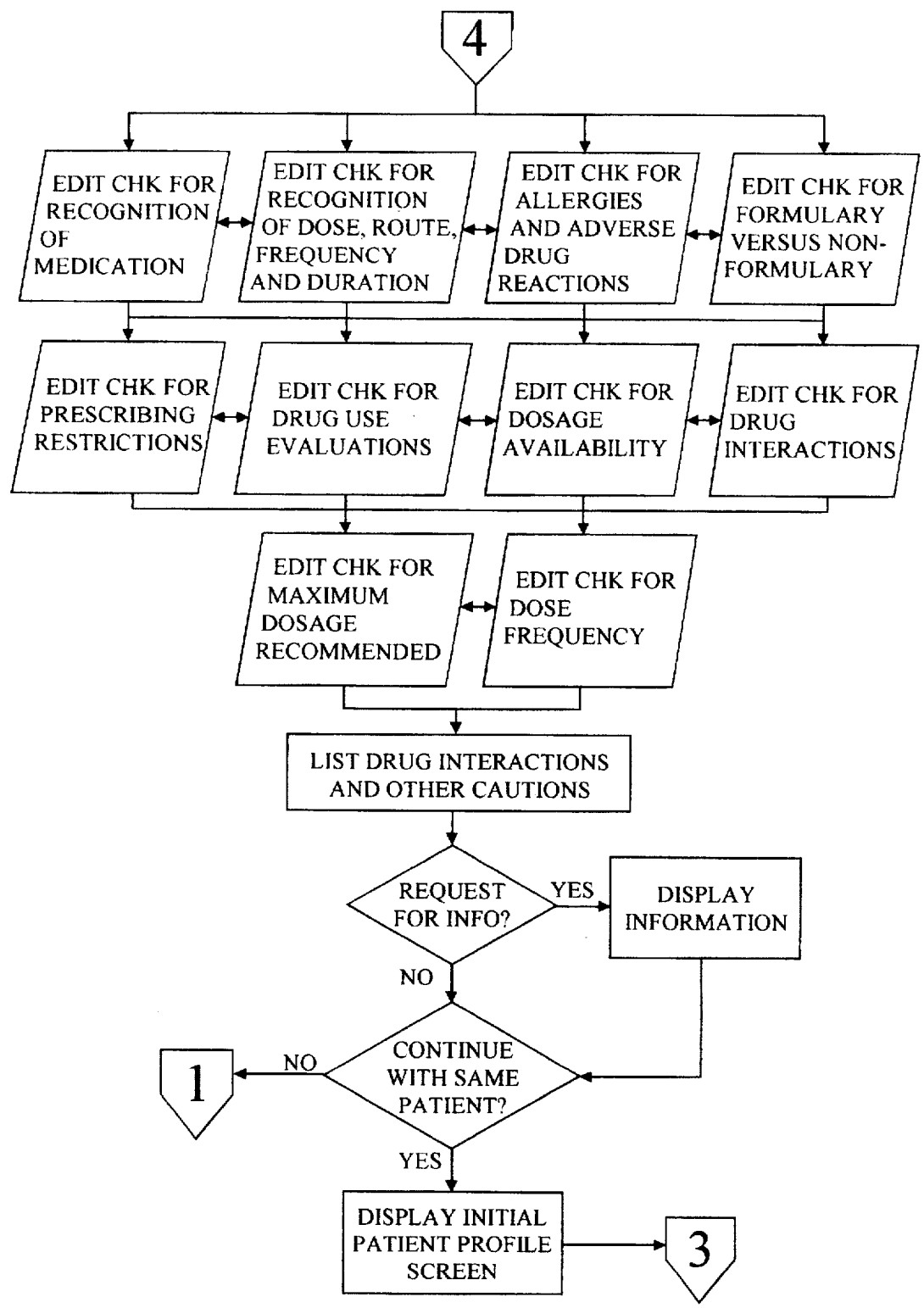
Figure 49E:
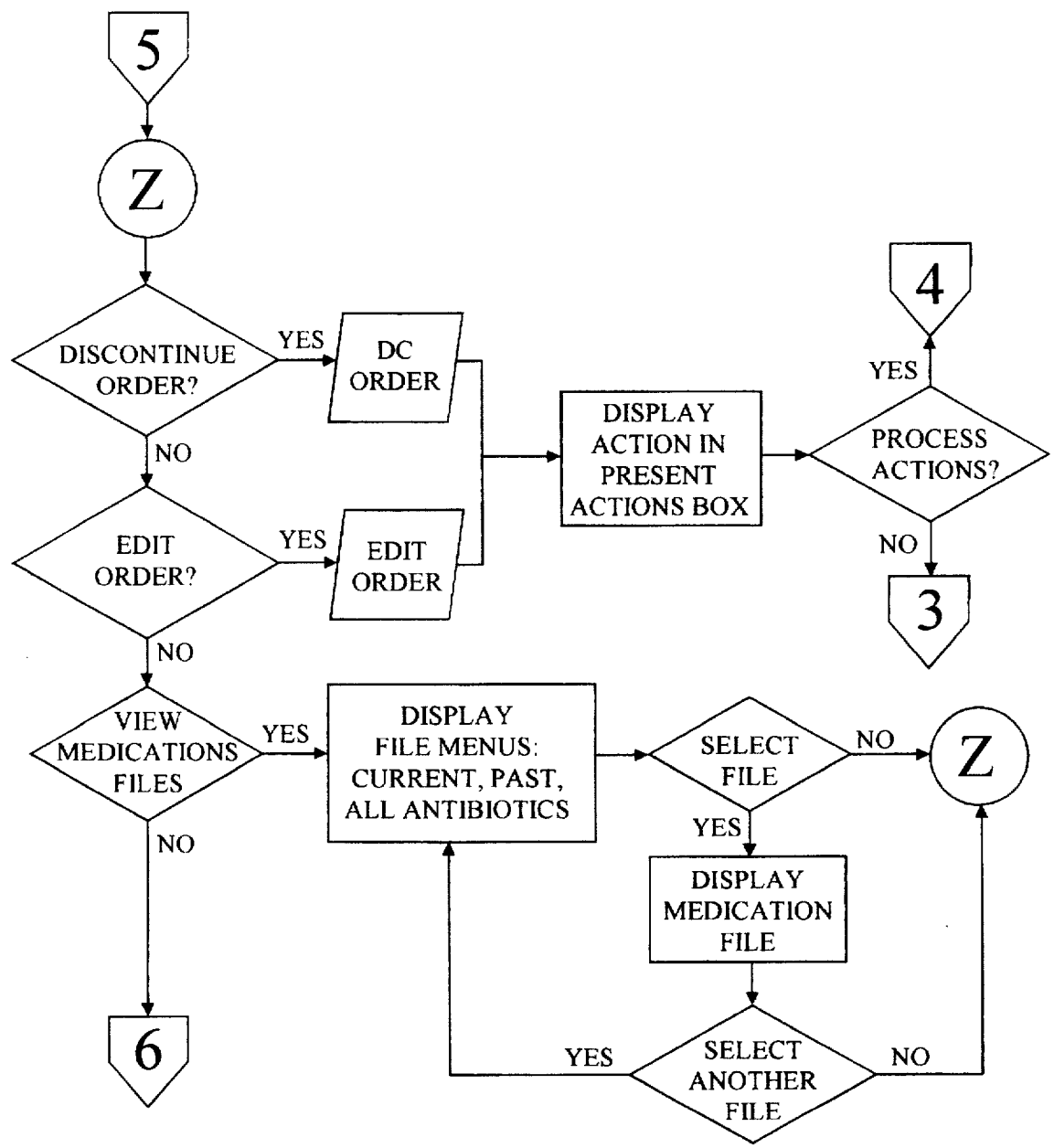
Figure 49F:
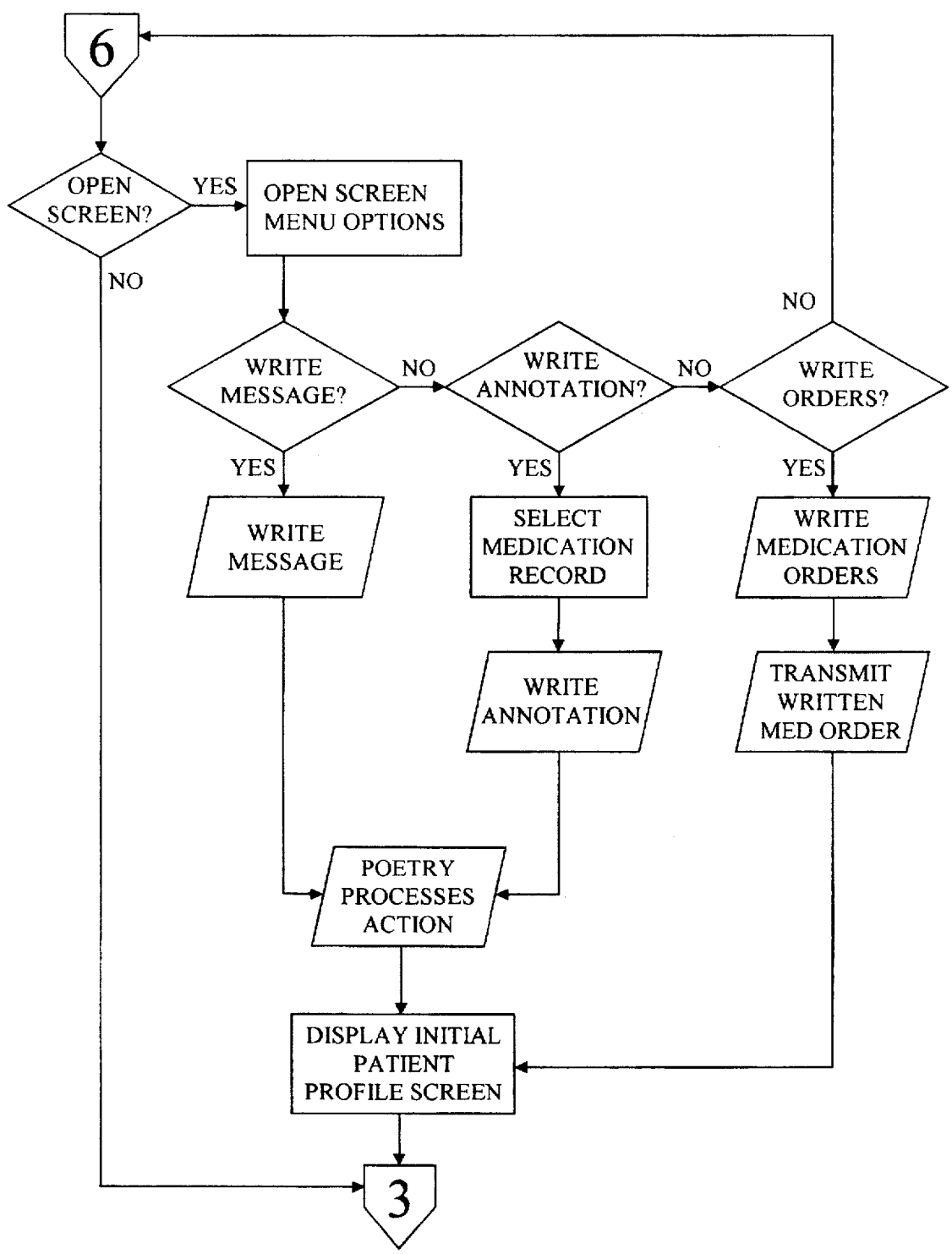
Figure 49G:
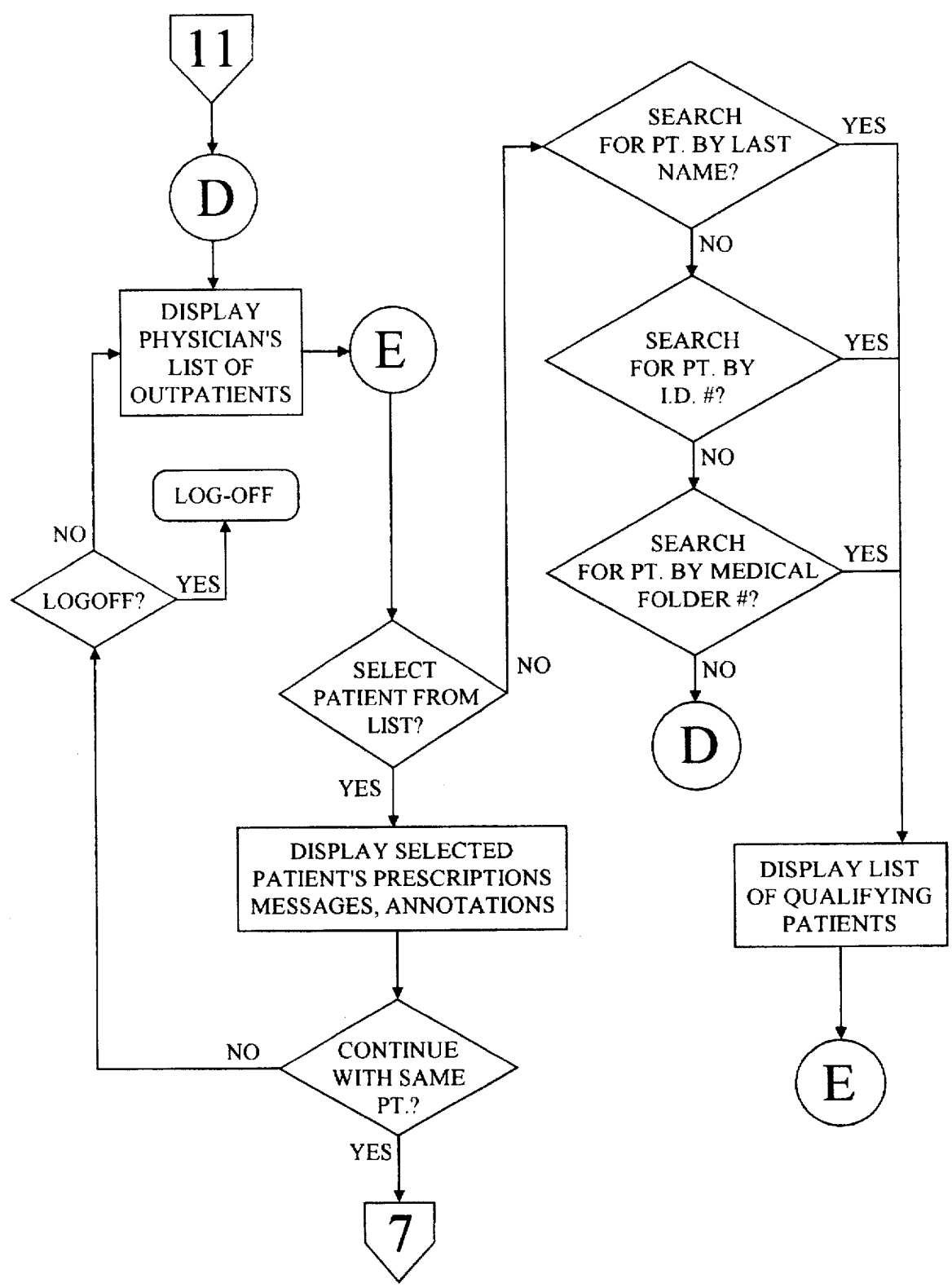
Figure 49H:
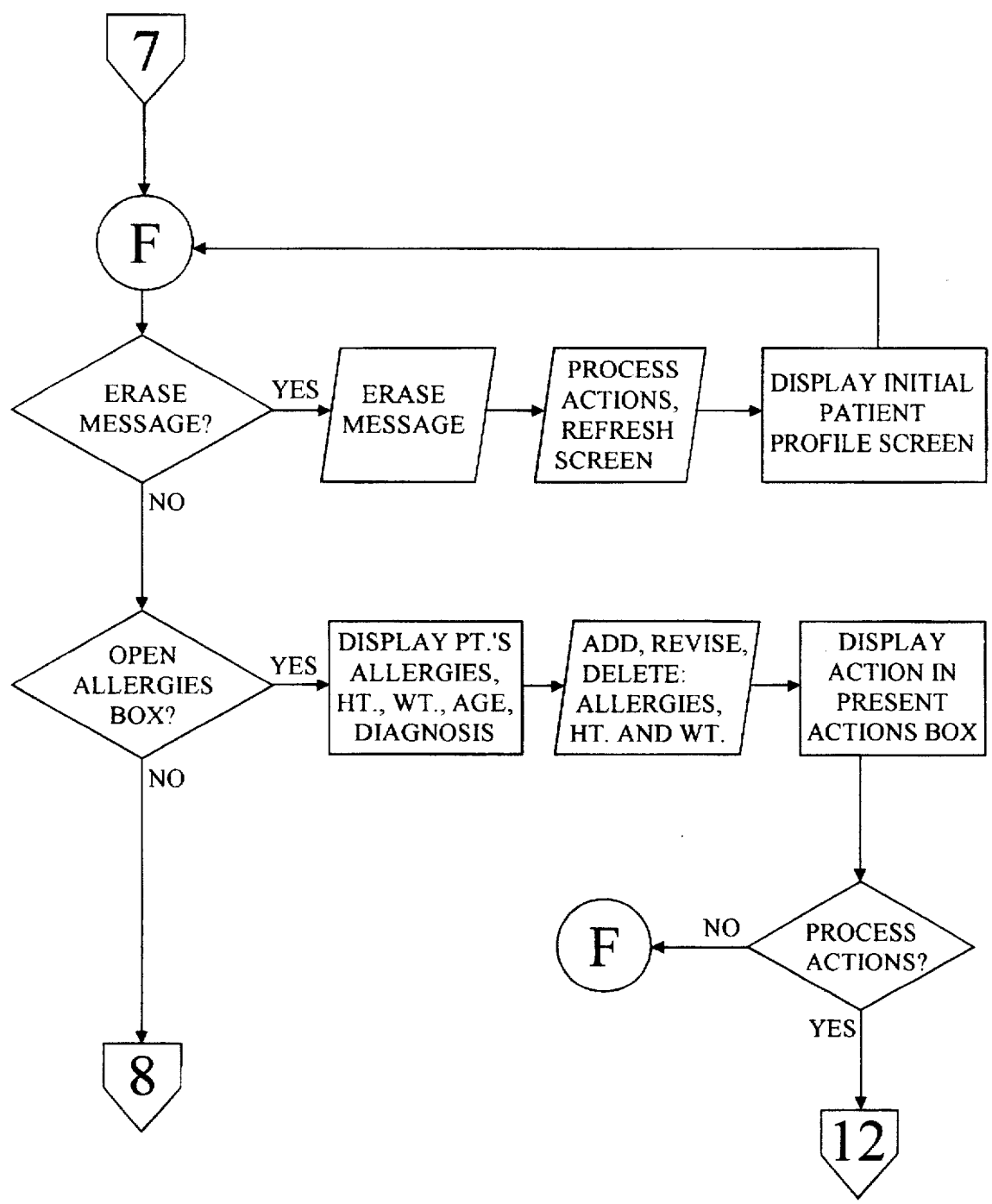
Figure 49I:
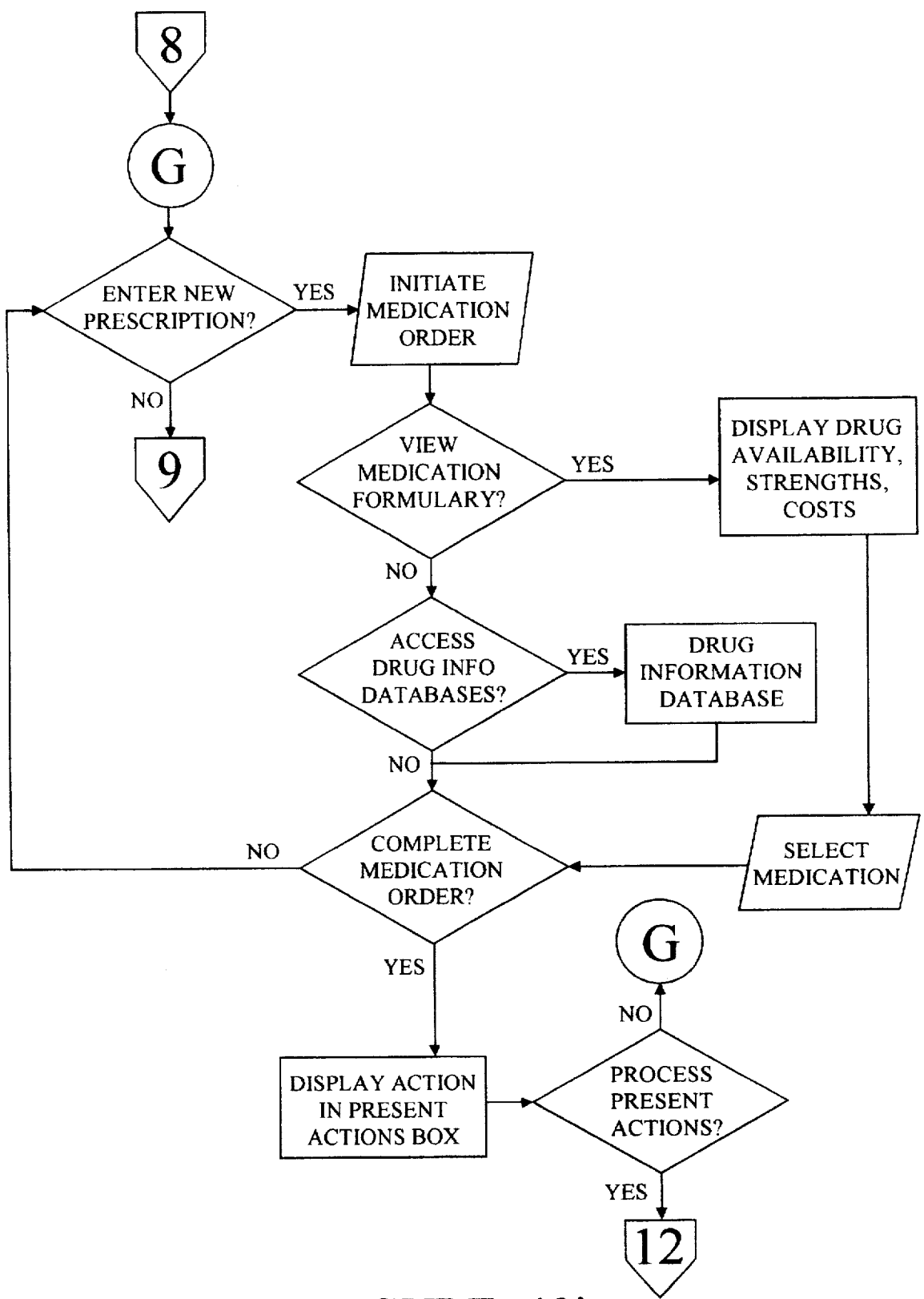
Figure 49J:
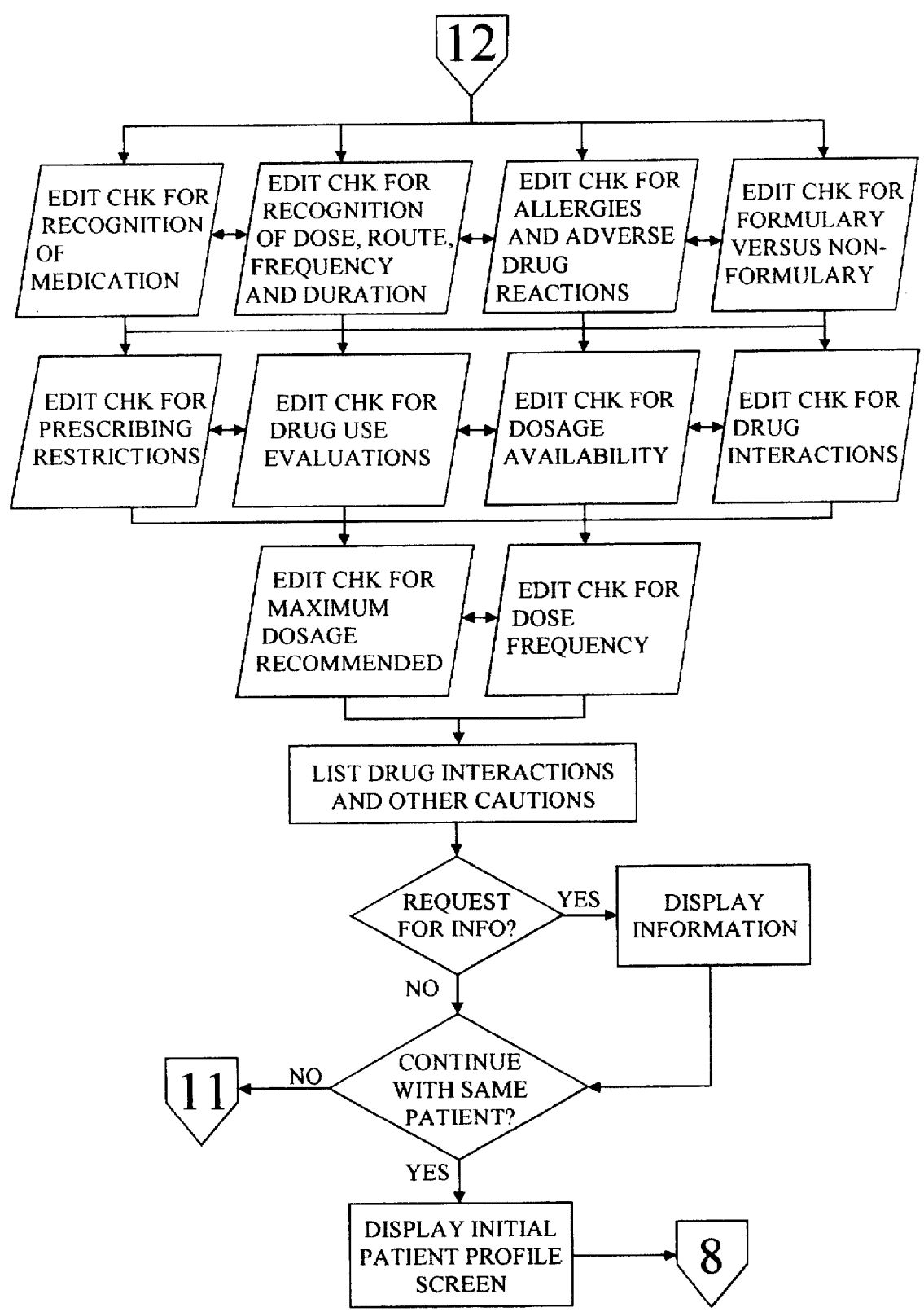
Figure 49K:
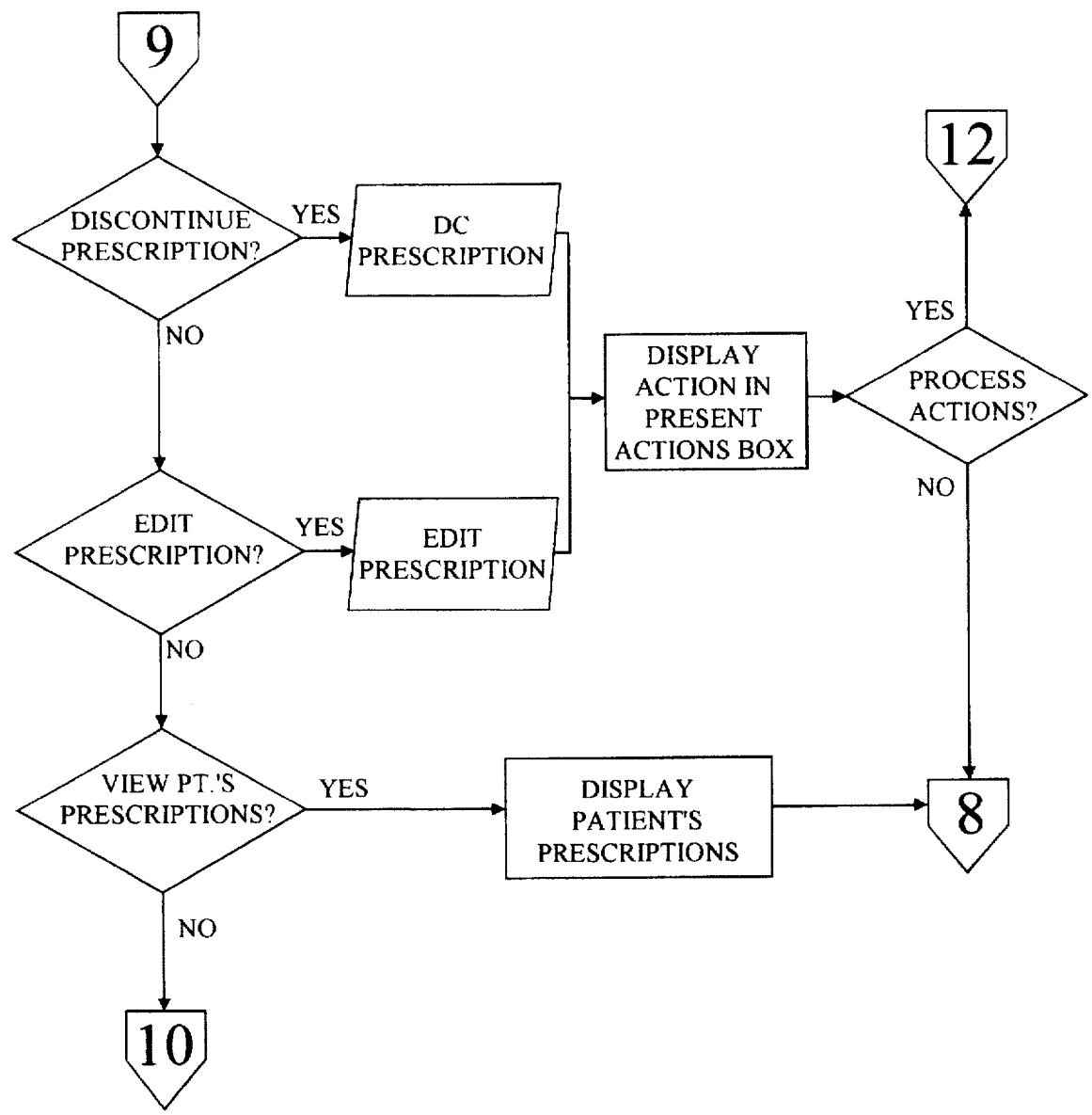
Figure 491:
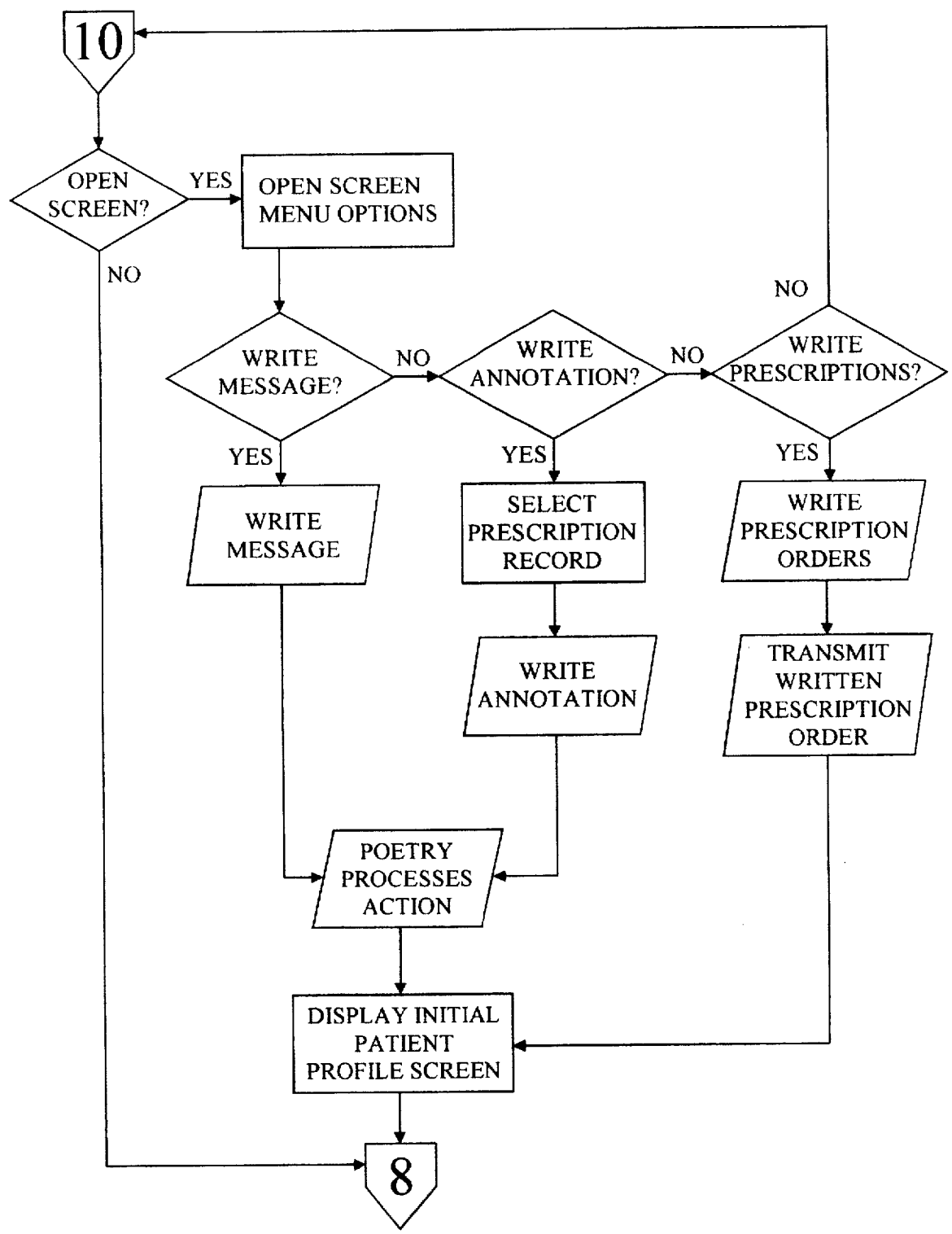

To write take-home medication orders, the user types or writes RX or speaks the "take-home meds" command as shown in screen 142, in FIG. 28. The user can then use the pen or mouse to select and highlight any current medication order from the scheduled or PRN medication lists. The selected medication order is copied onto the take-home medication ordering screen so that the user can revise the directions for take-home use and/or specify the quantity to dispense, as illustrated in screen 144, in FIG. 40. The user can also type or write new take-home medication orders instead of having to select the medication from the current scheduled or PRN medication lists. When the user is finished writing the take-home medication orders, the pen or mouse is used to select "POETRY SYSTEMS" 72 to close the take-home medication ordering screen and begin order processing.

To discontinue orders the user can speak the "DC" command or select the DC button 146 with the pen or mouse and any orders in the current scheduled or PRN medications list. The medication to discontinue are listed in the present actions box along with other new orders to serve as a summary or review before using the pen or mouse to select "POETRY SYSTEMS" 72 to close the ordering screen and begin order processing. The process of discontinuing orders is illustrated in FIG. 29.

The process for editing orders is shown in FIGS. 43–45. The user speaks the "EDIT" command or selects the EDIT button 152 with the pen or mouse and any order in the current scheduled or PRN medication lists. The screen then changes to screen 154 to display the selected medication order for editing as shown in FIG. 44. When the order is edited, the original order is discontinued and the changed order becomes a new order. These orders are listed in the present actions box, in FIG. 45, along with other new orders to serve as a summary or review before using the pen or mouse to select "POETRY SYSTEMS" 72 to close the screen and begin order processing.

When the user speaks the "LIST" command or selects the LIST button 78 with the pen or mouse, the screen changes to allow viewing of current, past and antibiotic medications orders as shown in screen 156, in FIG. 30. The viewing of current or past medication orders can be further broken down to scheduled only or PRN only retrievals. This is a view only function as illustrated in screen 158, in FIG. 31. The user can view any drug file by using the pen or mouse to select the current or past drug entry and then the LIST button 78, in FIG. 30. The screen changes to show a detailed profile of the drug order (See FIG. 63).

An additional feature of the hospital pharmacy system 10 of the present invention is the ability to record and maintain annotated information for each drug entry. This information includes patient outcome data, interventional data, recommendations and messages. This information is stored in the annotations file 162, in FIG. 1. This feature can be used to collect patient outcome data. Analysis of this data is important in assessing effectiveness of drug therapy. Managed care providers are incorporating ongoing measurements and evaluations of patient outcome data into designing drug prescribing guidelines. It is likely that all future drug formularies and prescribing recommendations and guidelines will be constructed around analysis and evaluation of patient outcome data. The present invention includes a simple way of entering and reviewing this information for individual medications. Patient outcome data can include past and present records listing monitoring measurements and achievements (or failure) of therapeutic endpoints (e.g. blood pressure measurements for anti-hypertensive drugs, blood glucose measurements for insulin and oral hypoglycemic drugs, infection eradication for antibiotics, etc.). Patient outcome data can also include information on drug side effects experienced during therapy and the historical record of dose changes made during the course of therapy. Interventions, recommendations, and other messages pertaining to an individual drug from physicians, pharmacists, nurses, respiratory therapists, or other clinicians can also be recorded.

All users have the ability to write an annotation pertaining to a selected drug file by using the pen or mouse to select the OPEN button 68 on the screen, in FIG. 10. In response, a free format screen 70 appears for the user to specify whether this is a patient mailbox message, a medication order or a drug file annotation as shown in FIG. 11. To add an annotation to a current drug's file, the user selects the annotation button 75 and the corresponding drug from the SCHEDULED meds 62 or the PRN medications 64 (See FIG. 61). The annotation is written, as seen in the example on FIG. 62. When the annotation is complete the user selects "POETRY SYSTEMS" 72 and the free format open screen will close and the written annotation will be sent to the annotations file for the selected drug (See FIG. 63). Annotations can also be added to a drug that has been discontinued by first using the LIST button 78 to recall and select the discontinued drug, and then the OPEN 68 button and annotation button 75. Examples of annotations include outcome evaluators, monitoring factors, recommendations and other specific notes pertaining to individual drugs.

An additional safety net feature of the present invention is an ongoing drug and dosing assessment based on diagnosis (e.g., end stage renal failure, pregnancy) and current laboratory data performed by function 166, in FIG. 1, and illustrated in screen 168, in FIG. 50. Imported laboratory data reflecting renal/kidney and hepatic/liver function and metabolic/electrolyte status will be continuously evaluated and a message will appear if drug dose adjustments, changes or discontinuations should be considered. Similar considerations will be evaluated for pregnant and lactating women.

This information is available to the relational databases 160. This creates a dynamic environment for drug and dosing assessments utilizing current measurements and trends of important laboratory data and diagnostic information.

The system is also capable of accessing drug information databases. The user enters the name of the drug and an asterisk (*) as shown in FIG. 47. This triggers access to the available drug information databases to import information on the specified drug (See FIG. 48). In addition, a database is also available to provide drug information for the layperson. Information from these databases can be printed at any time.

Referring to FIG. 1, the outpatient/clinic module 170 in accordance with the present invention is shown. Essentially, the features of the interactive medication system 10 with the inpatient module 13 are shared by the system with the outpatient/clinic module 170. All of the system features are the same in regard to the interactive screen format for entering prescriptions and retrieving information. Both will accept simplified and customary styles for medication prescribing. Bi-directional interaction and communication from the order reformatter and interpreter 136 are the same, as are all "safety net" features. There is a "seamless" interface to the preexisting hospital pharmacy system 12 and access to drug records and other pertinent patient specific information such as allergies, adverse drug reaction reports, and all drug file annotations, including recommendations, therapeutic interventions, and other documentation. A unique system feature of the outpatient/clinic pharmacy system 170 is the direct transmission of prescriptions. A modem or fax unit will process and transmit all complete prescription(s) to designated outpatient, clinic or retail pharmacies 174. Direct order entry is possible.

In addition, bidirectional communication is available from retail/outpatient/clinic pharmacies 174 and other off-site locations 176 (e.g., home care agencies, nursing homes, chronic care or skilled nursing facilities, same day surgery suites, prison wards) within the Poetry System 10. These pharmacies and off-site locations will have access to all available information and functional features of the Poetry System 10. Furthermore, bidirectional communication from retail/outpatient/clinic pharmacies and off-site locations can be used to transmit drug file annotations and patient-related messages. From pharmacies, authorization can be verified for prescription refills and controlled substances. For off-site locations, form-based checklists and other routine task requirements (e.g., drug evaluations and monitoring) can be completed and recorded from different screens available in the Poetry System 10.

Patient demographic data such as name, address, telephone number, date of birth, sex, diagnosis, allergies, height, weight, medical folder/record number, and insurance plan or managed care provider information are collected through a patient information interface with existing office hospital system (e.g., ADT/office interface) or can be entered directly into the system.

Patient selection utilizing the outpatient/clinic module 170 proceeds in a manner similar to that with the inpatient module 13. Patients can be selected by name or medical folder/record number or from a list of patients scheduled to be seen that day. FIG. 51 shows the opening screen of the outpatient/clinic pharmacy module with the ACTIVE PRESCRIPTIONS 90 window. All active prescriptions, including both scheduled and PRN (as needed) medications are listed together.

A window to access INACTIVE PRESCRIPTIONS 91 is also available. To view inactive prescriptions, the user selects the INACTIVE PRESCRIPTIONS 91 box with the pen or mouse. As shown in FIG. 67, a window opens and lists all inactive prescriptions with respective start and stop dates. By first selecting the inactive prescription with the pen or mouse and then selecting the LIST button 78 (See FIG. 68), a window is opened to view additional information such as the initiating physician, the physician that stopped the prescription, start and stop dates, a detailed dosing history, and any annotations or comments included with this prescription file (See FIG. 69).

Messages can be communicated within the system 10 configured with the outpatient/clinic module 170, from outpatient, clinic or retail pharmacies 174 or other off-site locations 176. FIG. 51, the opening screen for the outpatient/clinic pharmacy system 170, illustrates the message window 89. FIG. 52 shows examples of messages sent from a retail pharmacy and a physician. All or selected messages relating to clinic or office patients can be printed. These messages can be printed as soon as transmissions are received in the office or they can be stored for printing at a convenient time.

Figure 53:
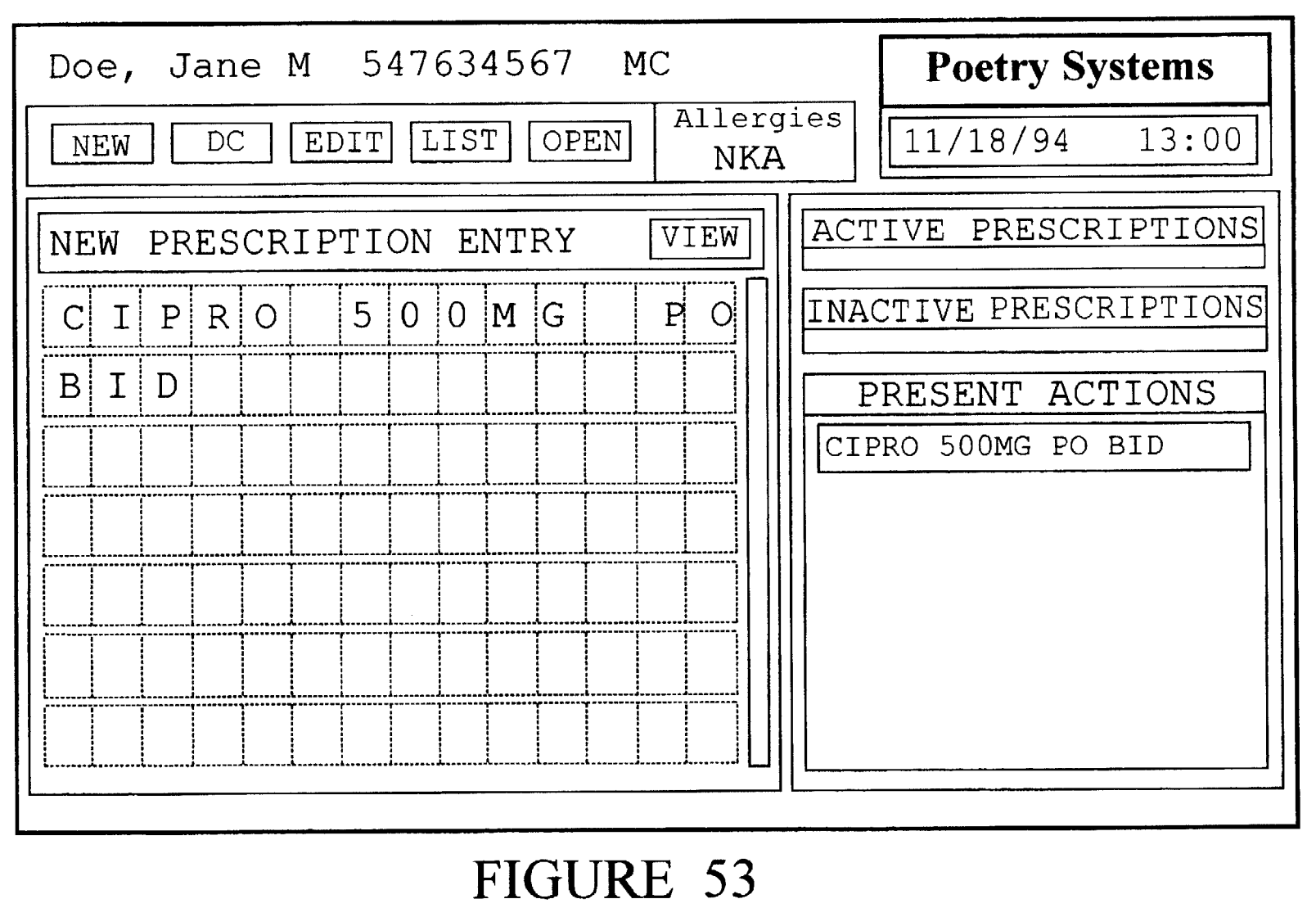

Based on the patient's insurance code or managed care program, the system will automatically route all prescriptions through the appropriate drug formularies for those programs and files listing program-specific prescribing restrictions (i.e., approved prescribing indications and dispensing quantities). When appropriate, screen selections will be available to the prescriber for requesting special treatment authorization for non-formulary drugs. Required information relating to the approval process for special treatment authorization (e.g., previous medications, laboratory data, microbiological data) can be collected and printed from the Poetry System 10. FIG. 60 shows the new prescription entry screen and FIG. 53 shows an example of prescribing a non-formulary drug for a patient with Medicaid (Medi-Cal in California) insurance. FIG. 54 illustrates the message screen that is presented and the selections given to the user. In this case, the user can cancel the order or process the order under specific circumstances and requirements. In another example of non-formulary prescribing, as seen in FIG. 56, the user is presented with a message window with several options including canceling the prescription, processing under specific circumstances or substituting the initial non-formulary drug selection with another formulary drug of the same pharmacologic class, as illustrated in FIG. 57. Selection of one of the substitute choices returns the user to the new prescription entry screen with the substitute drug already entered (See FIG. 58).

Annotations can be written into selected prescription files. FIG. 59 shows a written example. Annotations can include records for evaluation compliance (e.g., refill information), monitoring outcome measures or therapeutic endpoints, and other pertinent patient and prescription information (see annotations window 92, in FIG. 55).

Figure 64:
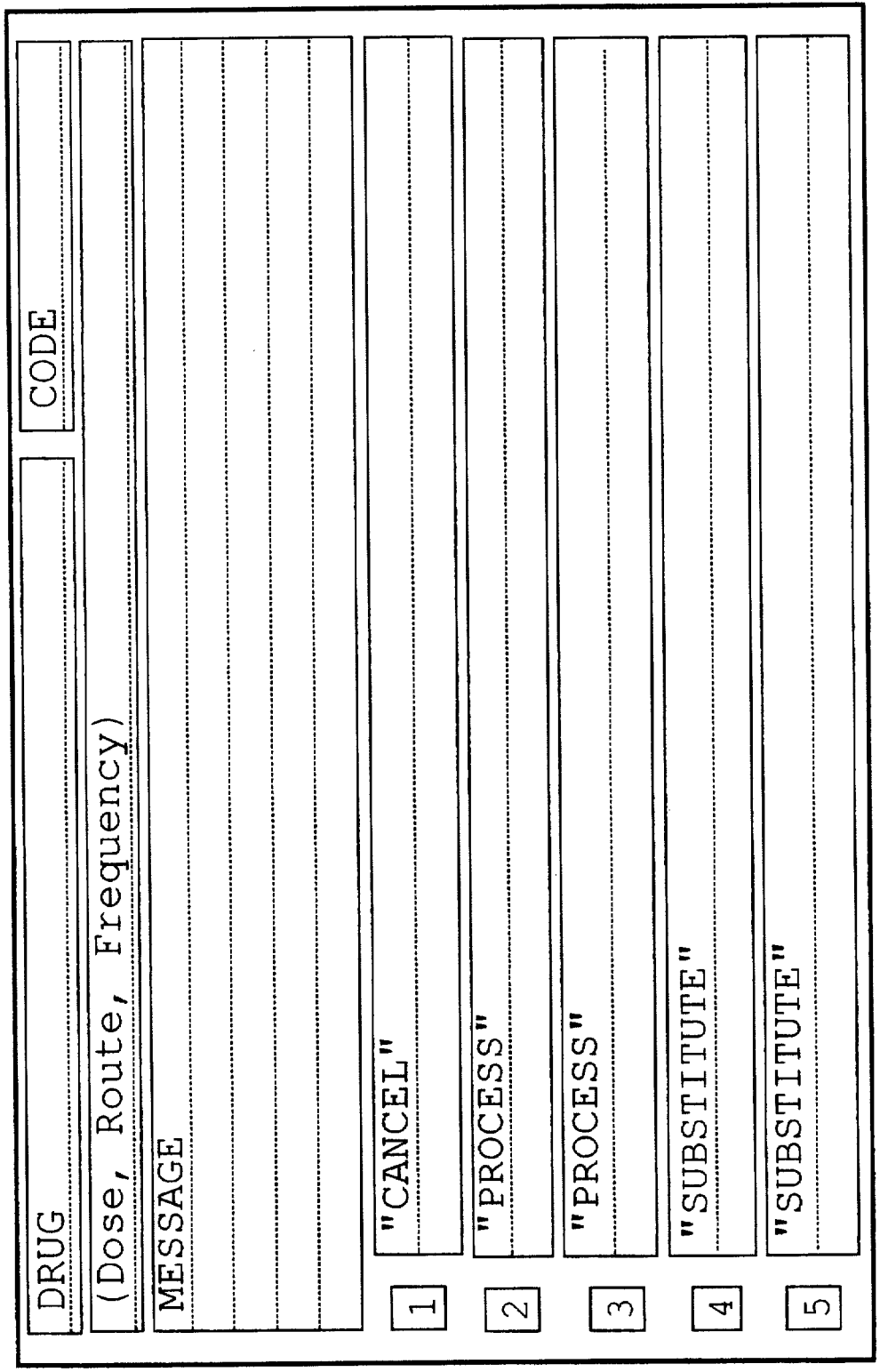
FIG. 64 depicts the message screen format accessed through the table/file maintenance program utilizing the present invention.

A table/file maintenance interface 22, in FIG. 1, is also available. This allows for the access to a set of POETRY SYSTEM relational databases 160. Appropriate database management can proceed with input including formulary updates, insurance and managed care coding, prescribing restriction updates, message and order set creation, drug interactions updates, and revising data for pharmacokinetics drug profiling. The table/file maintenance interface 22 will have a standard format for data and information entry. For example, a message can be entered using the server message screen format shown in FIG. 64. The drug and/or code will trigger the message that will present the user with several selections. The "CANCEL" selection will discontinue the drug order or prescription. The "PROCESS" selection will process the order as written. The "SUBSTITUTE" selection will list all drugs (in quotations) in boxes. FIG. 65 shows the construction of a non-formulary message to be transmitted when the antibiotic, ciprofloxacin, is prescribed for an outpatient with Medi-caid (Medi-CAL in California) insurance. Prescribing that medication, in FIG. 53, triggers the message screen to appear, in FIG. 54. The user can then cancel or process the order. FIG. 66 shows the creation of a message for the antihypertensive drug, accupril, when prescribed for an outpatient with Medi-CAL insurance. In addition to the cancel and process entries there is a selection for substitution with drugs in quotation marks. When this drug is prescribed, in FIG. 56, the message appears, in FIG. 57, and when the user selects the substitute drug option, captopril, a new order entry screen appears, in FIG. 58.

Reports regarding information within or between patient records can be generated from the reports interface. Access to all information in these records will be available. A wide variety of reports will be available. For example, a daily printout can be generated listing all patients lacking completion of allergy information, height, weight or diagnosis in their individual profiles. Workload (i.e., the number and variety of orders entered) and cost information can also be retrieved. Drug Use Evaluation (DUE) and Medication Use evaluation (MU) information can be generated. This information can be used to retrospectively compare and evaluate the use and conditions for use of different drugs. For example, reports will be available listing the use of a particular medication over a specified time period. Similar information can be collected regarding a particular physician. Combinations of different medications, or medications prescribed in patients with specific laboratory values can also be evaluated. Another example would be a report that collects information on medication(s) use in patients of a certain age, with a specific diagnosis, over a given time period.

Referring now to FIGS. 49A–49L, a series of flow charts illustrating the operation of the Poetry System 10 in accordance with the preferred embodiment is shown. The following is a brief description of the different flow diagrams.

DESCRIPTION OF SYSTEM FLOWS

FIG. 49(a)

A user signs onto either the POETRY SYSTEMS Hospital Pharmacy module or the Outpatient/Clinic module; access to either module is based on the user's ID (sign-on code).

Continuing with the Hospital Pharmacy module, if the user is a physician, that physician's inpatients are displayed on the patient selection screen. The physician may select a patient from his or her list or may search for a patient by name, medical record number, nursing station/unit or room/bed number.

If the user is not a physician, a patient selection screen is displayed allowing the user to search for a patient by name, medical record number, nursing station/unit or room/bed number.

A list of qualifying patients is displayed. The list is refined as more specific search criteria (e.g., more letters of the patient's name or letters and numbers of the patient's nursing station/unit) is entered into the system.

The selected patient's profile screen is displayed.

FIG. 49(b)

A patient's profile screen provides the user with different functions:

erase messages—the user may read any patient-specific messages and then erase the message(s); POETRY processes this action immediately and refreshes the patient profile screen.

countersign orders—if the user is a physician, orders needing to be countersigned are displayed, allowing the physician to electronically sign the patient's order(s); POETRY processes this action immediately and refreshes the patient profile screen; non-physician users do not see this display nor do they have this function.

specify allergies—the user may view the patient's allergies, height and weight, age and diagnosis and may add to, revise or delete the patients' allergies or height and weight or diagnosis; these actions will list in the present actions list and may be processed at anytime before another patient is selected or before the user signs off the system.

renew medication order—when a physician renews a medication order, the action is listed in the present actions list and may be processed at anytime before another patient is selected or before the user signs off the system; non-physician users must specify the physician authorizing the order renewal and the action is listed in the present actions list and may be processed at anytime before another patient is selected or before the user signs off the system.

FIG. 49(c)

enter new orders—the user may enter a new medication order completely (medication and directions for administration) or may view the drug formulary which displays drug availability, strengths and costs for the medication selected; the user is also given the ability to access drug information databases; the user completes the order after selecting the medication from the formulary; new medication orders are listed in the present actions list and may be processed at anytime before another patient is selected or before the user signs off the system.

FIG. 49(d)

process present actions—POETRY processes all actions in the present actions list and checks for:

recognition of medication ordered, dose, route, frequency and duration allergies and adverse drug reactions formulary vs. non-formulary drug items prescribing restrictions dosage availability drug interactions maximum dosage recommended dose frequency drug use evaluations POETRY lists all drug interactions and other cautions.

The user may request for more information regarding the drug interactions and other cautions.

If the user chooses to continue with the same patient, the initial patient profile screen is displayed.

The user may continue with a new patient or the user may logoff.

FIG. 49(e)

discontinue order—the user may discontinue a current or active medication order and the action is listed in the present actions list and may be processed at anytime before another patient is selected or before the user signs off the system.

edit order—the user may edit a current or active medication order and the action is listed in the present actions list and may be processed at anytime before another patient is selected or before the user signs off the system.

view patient's medications—the user may view all medication orders for this patient.

FIG. 49(f)

open screen—the user is given three option in the open screen function:
- write message—the user may write a message pertaining to this patient; POETRY processes this action immediately and refreshes the patient profile screen.
- write annotation—the user selects the medication record to write an annotation; POETRY processes this action immediately and refreshes the patient profile screen.
- write orders—the user may write a medication order(s) which will transmit immediately to the hospital pharmacy system; POETRY refreshes the patient profile screen.

FIG. 49(g)

In the Outpatient/Clinic module, the physician's outpatient are displayed on the patient selection screen. The physician may select a patient from his or her list or may search for a patient by name, identification number, or medical folder number.

A list of qualifying patients is displayed. The list is refined as more specific search criteria (e.g., more letters of the patient's name or more numbers of the patient's identification number) is entered into the system.

The selected patient's profile screen is displayed, showing the patient's prescriptions, messages and annotations.

FIG. 49(h)

A patient's profile screen provides the user with different functions:
- erase messages—the user may read any patient-specific messages and then erase the message(s); POETRY processes this action immediately and refreshes the patient profile screen.
- specify allergies—the user may view the patient's allergies, height and weight, age and diagnosis and may add to, revise or delete the patients' allergies or height and weight or diagnosis; these actions will list in the present actions list and may be processed at anytime before another patient is selected or before the user signs off the system.

FIG. 49(i)

enter new prescriptions—the user may enter a new prescription completely (medication and patient instructions) or may view the drug formulary which displays drug availability, strengths and costs for the medication selected; the user is also given the ability to access a drug information database; the user completes the prescription after selecting the medication from the formulary; new prescriptions are listed in the present actions list and may be processed at anytime before another patient is selected or before the user signs off the system.

FIG. 49(j)

process present actions—POETRY processes all actions in the present actions list and checks for:
- recognition of medication ordered, dose, route, frequency and duration
- allergies and adverse drug reactions
- formulary vs. non-formulary drug items
- prescribing restrictions
- dosage availability
- drug interactions
- maximum dosage recommended
- dose frequency
- drug use evaluation POETRY lists all drug interactions and other cautions.

The user may request for more information regarding the drug interactions and other cautions.

If the user chooses to continue with the same patient, the initial patient profile screen is displayed.

The user may continue with a new patient or the user may logoff.

FIG. 49(k)

discontinue prescription—the user may discontinue an active prescription and the action is listed in the present actions list and may be processed at anytime before another patient is selected or before the user signs off the system.

edit prescription—the user may edit an active prescription and the action is listed in the present actions list and may be processed at anytime before another patient is selected or before the user signs off the system.

view patient's prescriptions—the user may view all active and inactive prescriptions for this patient.

FIG. 49(l)

open screen—the user is given three option in the open screen function:
- write message—the user may write a message pertaining to this patient; POETRY processes this action immediately and refreshes the patient profile screen.
- write annotation—the user selects the prescription record to write an annotation; POETRY processes this action immediately and refreshes the patient profile screen.
- write prescription—the user may write a prescription(s) which will transmit immediately to the retail or outpatient/clinic pharmacy; POETRY refreshes the patient profile screen.

Those skilled in the art can appreciate that other advantages can be obtained from the use of this invention and modifications can be made without departing from the true spirit of the invention after studying the specifications, drawings and following claims.

What is claimed is:

1. A system for prescribing medication for a patient, said system comprising:
    means for permitting a user to identify said patient;
    database containing health and medication information regarding said patient;
    means for automatically accessing said database and displaying to said user a list of all of the currently prescribed medications for said patient;
    means for accepting and processing information regarding said medication prescriptions for said patient from the user including interpreter and reformatter means for processing said information received in a random sequence, wherein said information is received in a random sequence, and wherein said information includes at least one medication identifier and information selected from the group consisting of: recognition of medication ordered, recognition of medication dosage, recognition of medication route, recognition of medication frequency, recognition of medication duration, recognition of medication quantity, formulary drug items, non-formulary drug items, restrictions on prescriptions, dosage availability, maximum dosage recommended for said patient, dosage frequency, and drug use evaluations; and
    means for communicating said medication prescription to a pharmacy.

2. The system of claim 1 further comprising means for receiving and storing messages relating to said patient, said messages being automatically displayed to said user upon the identification of said patient by said user.

3. The system of claim 2 further comprising means for permitting medical personnel to enter messages to said user.

4. The system of claim 1 wherein said means for permitting a user to identify a patient includes search assisting means for permitting the user to search for said patient by a plurality of identifiers.

5. The system of claim 4 wherein said identifier is the patient's name.

6. The system of claim 4 wherein said identifier is the patient's location or ID number.

7. The system of claim 1 wherein said means for accepting and processing medication prescriptions comprises a computer display screen having a field for entering information regarding the prescribed medications.

8. The system of claim 7 wherein said prescribed medication can be selected by one of a plurality of descriptions including, brand or generic names or abbreviations.

9. The system of claim 1 wherein said means for accepting and processing medication prescription further comprises means for modifying previous medication prescriptions.

10. The system of claim 1 further comprising voice recognition unit for permitting said user to communicate with said system by means of verbal inputs.

11. The system of claim 1 further comprising pen interface for permitting said user to communicate with said system by writing on said screen with a pen.

12. The system of claim 1 wherein said information is received by more than one of the following means: voice, keyboard, pen and mouse.

13. The system of claim 1 further comprising:
database containing health and medication information regarding medications and said patient; and
means for alerting said user to potentially adverse situations as a result of said prescribed medications, based on information in said database.

14. The system of claim 13 wherein said adverse situation is an allergic reaction to said prescribed medication.

15. The system of claim 13 wherein said adverse reaction is an interaction between two or more prescribed medications.

16. The system of claim 1 further comprising:
said medication prescriptions comprising a description of a product, dosage and route of administration;
means for automatically determining product formulation and compounding based on said descriptions; and
means for communicating said prescription to a pharmacy.

17. The system of claim 16 wherein said means for automatically determining product formulation further comprises means of processing complex orders.

18. The system of claim 17 wherein said complex orders comprise a medication taper.

19. The system of claim 16 further comprising means for calculating pharmacokinetics dosing based on said medication prescription.

20. The system of claim 1 further comprising:
database for storing information relating to a plurality of patients;
administration interface means for receiving and storing administrative messages relating to predetermined situations; and
means for automatically displaying one of said messages to said user when said medication prescription represents the occurrence of one of said predetermined situations.

21. The system of claim 20 wherein said predetermined situation is the prescribing of medication which is not in the available formulary.

22. The system of claim 20 wherein said predetermined situation is the prescribing of a medication which is not recommended.

23. The system of claim 22 further comprising means for displaying alternatives to the non-recommended medication.

24. The system of claim 20 wherein said database includes ongoing lab data with respect to said patient and further wherein said messages include recommended drug changes based on said ongoing lab data.

25. The system of claim 1 further comprising:
an interactive environment for facilitating a user in prescribing said medications and said patient from said user;
output means for communicating to said user relevant information relating to said prescribed medications and said patients; and
means for permitting said user to modify said prescribed medications based on said information received from said output means.

26. The system of claim 25 wherein said output means communicates to said user messages regarding said prescribed medication and potential adverse reactions.

27. The system of claim 25 further comprising table/file maintenance means for permitting the updating of information communicated by said output means.

28. The system of claim 1 or claim 13 or claim 16 or claim 20 or claim 25 wherein said interpreter and reformatter means for processing said information received in a random sequence includes means for receiving said information as a single input.

* * * * *